United States Patent
Wagle et al.

(10) Patent No.: US 6,960,605 B2
(45) Date of Patent: *Nov. 1, 2005

(54) THIAZOLE, IMIDAZOLE AND OXAZOLE COMPOUNDS AND TREATMENTS OF DISORDERS ASSOCIATED WITH PROTEIN AGING

(75) Inventors: Dilip Wagle, Pune (IN); Sarah Vasan, New York, NY (US); Jack Egan, New York, NY (US)

(73) Assignee: Alteon, Inc., Parsippany, NJ (US)

( * ) Notice: Subject to any disclaimer, the term of this patent is extended or adjusted under 35 U.S.C. 154(b) by 342 days.

This patent is subject to a terminal disclaimer.

(21) Appl. No.: 09/766,547

(22) Filed: Jan. 19, 2001

(65) Prior Publication Data

US 2002/0022622 A1 Feb. 21, 2002

Related U.S. Application Data

(60) Provisional application No. 60/183,274, filed on Feb. 17, 2002, provisional application No. 60/259,237, filed on Jan. 2, 2001, provisional application No. 60/259,239, filed on Jan. 2, 2001, provisional application No. 60/176,995, filed on Jan. 19, 2000, provisional application No. 60/259,291, filed on Dec. 29, 2000, and provisional application No. 60/259,107, filed on Dec. 29, 2000.

(51) Int. Cl.$^7$ .......................... A61K 31/425; A61P 9/00
(52) U.S. Cl. ...................................... 514/365; 514/367
(58) Field of Search ..................... 514/365, 367, 514/396, 374; 548/235, 204, 560

(56) References Cited

U.S. PATENT DOCUMENTS

| | | | |
|---|---|---|---|
| 5,192,781 A * | 3/1993 | Bru-Magniez et al. | 514/365 |
| 5,326,779 A | 7/1994 | Ulrich et al. | |
| 5,358,960 A | 10/1994 | Ulrich et al. | |
| 5,853,703 A | 12/1998 | Cerami et al. | 424/53 |
| 6,297,266 B1 | 10/2001 | Alig et al. | 514/370 |
| 6,320,054 B1 | 11/2001 | Alig et al. | 548/196 |
| 6,596,744 B2 * | 7/2003 | Wagle et al. | 514/365 |

FOREIGN PATENT DOCUMENTS

| | | |
|---|---|---|
| WO | WO 92/14704 | 9/1992 |
| WO | WO 97/06819 | 2/1997 |

OTHER PUBLICATIONS

Foulkes et al., 1996, CAS: 102570.*
Partial European Search Report for EP 01904934.5. Mailed Apr. 17, 2003.

* cited by examiner

*Primary Examiner*—Rita Desai
*Assistant Examiner*—Robert Shiao
(74) *Attorney, Agent, or Firm*—Mintz, Levin, Cohn, Ferris Glovsky and Popeo, PC; Ivor R. Elrifi, Esq.

(57) ABSTRACT

Provided are, among other things, compounds of formula I or IA,

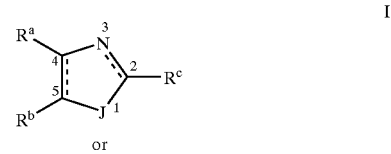

I

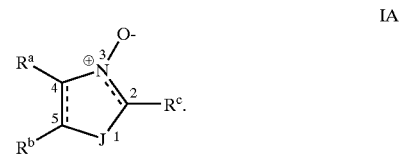

IA

Also provided are methods of treatment with such compounds.

10 Claims, No Drawings

THIAZOLE, IMIDAZOLE AND OXAZOLE COMPOUNDS AND TREATMENTS OF DISORDERS ASSOCIATED WITH PROTEIN AGING

This applications claims the priority of the following applications: Application No. 60/176,995, filed 19 Jan. 2000; No. 60/183,274, filed 17 Feb. 2002; No. 60/259,291, filed 29 Dec. 2000; No. 60/259,237, filed 2 Jan. 2001; No. 60/259,107, filed 29 Dec. 2000; and No. 60/259,239, filed 2 Jan. 2001.

The present invention relates to methods for treating certain fibrotic diseases or other indications.

Glucose and other sugars react with proteins by a non-enzymatic, post-translational modification process called non-enzymatic glycosylation. At least a portion of the resulting sugar-derived adducts, called advanced glycosylation end products (AGEs), mature to a molecular species that is very reactive, and can readily bind to amino groups on adjacent proteins, resulting in the formation of AGE cross-links between proteins. Recently a number of classes of compounds have been identified whose members inhibit the formation of the cross-links, or in some cases break the cross-links. These compounds include, for example, the thiazolium compounds described in U.S. Pat. No. 5,853,703. As AGEs, and particularly the resulting cross-links, are linked to several degradations in body function linked with diabetes or age, these compounds have been used, with success, in animal models for such indications. These indications include loss of elasticity in blood vasculature, loss of kidney function and retinopathy. Now, as part of studies on these compounds, it has been identified that these compounds inhibit the formation of bioactive agents, such as growth factors and inflammatory mediators, that are associated with a number of indications. These agents include vascular endothelial growth factor (VEGF) and TGF [beta]. As a result, a number of new indications have been identified for treatment with agents that inhibit the formation of, or more preferably break, AGE-mediated cross-links. It is not unreasonable to infer that the effects seen are due to the removal of AGE-related molecules that provide a stimulus for the production or release of these growth factors. Removal of such molecules is believed to proceed in part due to the elimination of AGE-related cross-links that lock the AGE-modified proteins in place. Moreover, such compounds also reduce the expression of collagen in conditions associated with excess collagen production. Regardless of the mechanism, now provided are new methods of treating a number of indications.

SUMMARY OF THE INVENTION

In one embodiment, the invention relates to a method of treating or ameliorating or preventing an indication of the invention in an animal, including a human, comprising administering an effective amount of a compound of the formula I or IA,

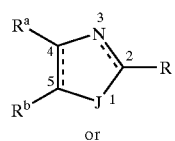

or

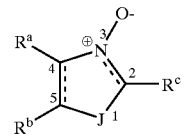

wherein the substituent groups are as defined below. In another embodiment, the compound administered is a compound of formula II,

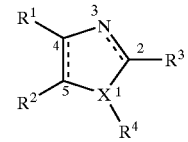

wherein the substituent groups are as defined below.

DETAILED DESCRIPTION OF THE INVENTION

In accordance with the present invention, a method and compositions are disclosed for, among other things, in an animal, treating the indications described below and (i) improving the elasticity or reducing wrinkles of the skin, treating (ii) diabetes or treating or preventing (iii) adverse sequelae of diabetes, (iv) kidney damage, (v) damage to blood vasculature, (vi) hypertension, (vii) retinopathy, (viii) damage to lens proteins, (ix) cataracts, (x) peripheral neuropathy, or (xi) osteoarthritis. Without being bound by theory, these effects are believed to related to the inhibition of formation of advanced glycosylation of proteins protein aging) and for breaking the cross-links that form between advanced glycosylation (glycation) endproducts (AGEs) or between AGEs and other proteins. The invention further relates to preventing or reversing advanced glycosylation endproducts and cross-linking caused by other reactive sugars present in vivo or in foodstuffs, including ribose, galactose and fructose.

In particular, the compositions comprise agents for inhibiting the formation of and reversing the pre-formed advanced glycosylation (glycation) endproducts and breaking the subsequent cross-links. While not wishing to be bound by any theory, it is believed that the breaking of the pre-formed advanced glycosylation (glycation) endproducts and cross-links is a result of the cleavage of alpha-dicarbonyl-based protein crosslinks present in the advanced glycosylation endproducts.

Certain of the agents useful in the present invention are members of the class of compounds known as thiazoles, others are imidazoles or oxazoles.

The compounds, and their compositions, utilized in this invention are believed to react with an early glycosylation product thereby preventing the same from later forming the advanced glycosylation end products that lead to cross-links, and thereby, to molecular or protein aging and other adverse molecular consequences. Additionally, they react with already formed advanced glycosylation end products to reduce the amount of such products.

The ability to inhibit the formation of advanced glycosylation endproducts, and to reverse the already formed advanced glycosylation products in the body carries with it significant implications in all applications where advanced glycation and concomitant molecular crosslinking is a serious detriment. Thus, in the area of food technology, for instance, the retardation of food spoilage would confer an obvious economic and social benefit by making certain foods of marginal stability less perishable and therefore more available for consumers. Spoilage would be reduced as would the expense of inspection, removal, and replacement, and the extended availability of the foods could aid in stabilizing their price in the marketplace. Similarly, in other industrial applications where the perishability of proteins is a problem, the admixture of the agents of the present invention in compositions containing such proteins would facilitate the extended useful life of the same. Presently used food preservatives and discoloration preventatives such as sulfur dioxide, known to cause toxicity including allergy and asthma in animals, can be replaced with compounds such as those described herein.

The present method has particular therapeutic application as the Maillard process acutely affects several of the significant protein masses in the body, among them collagen, elastin, lens proteins, and the kidney glomerular basement membranes. These proteins deteriorate both with age (hence the application of the term "protein aging") and as a consequence of diabetes. Accordingly, the ability to either retard or substantially inhibit the formation of advanced glycosylation endproducts, and to reduce the amount of cross-links formed between advanced glycosylation endproducts and other proteins in the body carries the promise for treatment of the complications of diabetes and aging for instance, and thereby improving the quality and, perhaps, duration of animal and human life.

The present agents are also useful in the area of personal appearance and hygiene, as they prevent, and reverse, the staining of teeth by cationic anti-microbial agents with anti-plaque properties, such as chlorhexidine.

In certain embodiments, the indications treated, ameliorated or prevented with the invention are those described or the agents are those described in parent applications No. 60/176,995, filed 19, Jan. 2000, No. 60/183,274, filed 17, Feb. 2000, No. 60/259,237, filed 29, Dec. 2000, No. 60/259, 237 filed 2, Jan. 2001, No. 60/259,107, filed 29, Dec. 2001 and No. 60/259,239 filed 2 Jan. 2001. These applications are incorporated herein in their entirety.

Substituents

For compounds of formulas I and IA,
a. J is oxygen, sulfur, or N—$R^d$;
b. the carbon 2 to nitrogen bond is a double bond except when $R^c$ is oxo;
c. the bond between carbons 4 and 5 is a single bond or a double bond;
d. $R^a$ and $R^b$ are
   1. independently selected from hydrogen, acylamino, acyloxyalkyl, alkanoyl, alkanoylalkyl, alkenyl, alkoxy, alkoxycarbonyl, alkoxycarbonylalkyl, alkyl, alkylamino, (C1–C3)alkylenedioxy, allyl, amino, ω-alkylenesulfonic acid, carbamoyl, carboxy, carboxyalkyl (which alkyl can be substituted with alkyloxyimino), cycloalkyl, dialkylamino, halo, hydroxy, (C2–C6)hydroxyalkyl, mercapto, nitro, sulfamoyl, sulfonic acid, alkylsulfonyl, alkylsulfinyl, alkylthio, trifluoromethyl, morpholin-4-yl, thiomorpholin-4-yl, piperidin-1-yl, piperazin-1-yl, Ar {wherein, consistent with the rules of aromaticity, Ar is $C_6$ or $C_{10}$ aryl or a 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N, each heteroaryl ring can be fused to a substituted benzene, pyridine, pyrimidine, pyridazine, or (1,2,3)triazine (wherein the ring fusion is at a carbon-carbon double bond of Ar)}, Ar-alkyl, ArO—, $ArSO_2$—, ArSO—, ArS—, $ArSO_2NH$—, ArNH, (N—Ar)(N-alkyl)N—, ArC(O)—, ArC(O)NH—, ArNH—(C(O)—, and (N—Ar)(N-alkyl)N—C(O)—, or together $R_1$ and $R_2$ comprise methylenedioxy-; or
   2. together with their ring carbons form a $C_6$- or $C_{10}$- aryl fused ring; or
   3. together with their ring carbons form a $C_5$–$C_7$ fused cycloalkyl ring having up to two double bonds including a fused double bond of the containing group, which cycloalkyl ring can be substituted by one or more of the group consisting of alkyl, alkoxycarbonyl, amino, aminocarbonyl, carboxy, fluoro, or oxo; or
   4. together with their ring carbons form a fused 5- or 6-membered heteroaryl ring, wherein the 6-membered heteroaryl ring contains one to three atoms of N, and the 5- membered heteroaryl ring contains from one to three atoms of N or one atom of O or S and zero to two atoms of N; or
   5. together with their ring carbons form a fused five to eight membered second heterocycle, wherein the fused heterocycle consists of ring atoms selected from the group consisting of carbon, nitrogen, oxygen, sulfur, and $S(O)_n$, wherein n is 1 or 2;
b. $R^d$ is alkyl, alkenyl, hydrogen, or Ar;
c. $R^c$ is
   1. oxo (when $\Delta^{2,3}$ is not present), or (when $\Delta^{2,3}$ is present) hydrogen, alkyl, alkylthio, hydrogen, mercapto, amino, amino($C_1$–$C_5$)alkyl, amino($C_6$ or $C_{10}$)aryl, or wherein the amino of the last three groups can be substituted with
      (a) Ar,
      (b) Ar—Z—, Ar-alkyl-Z—, Ar—Z-alkyl, Ar-amino-Z-, Ar-aminoalkyl-Z-, or Ar-oxyalkyl-Z-, wherein Z is a carbonyl or —$SO_2$—,
      (c) formyl or alkanoyl, or
      (d) up to two alkyl,
   2. —$NHC(O)(CH_2)_n$—D—$R^eR^f$, wherein D is oxygen, sulfur or nitrogen, wherein where D is nitrogen n is 0, 1 or 2, but when D is oxygen or sulfur n=1 or 2, and $R^f$ is present only when D is nitrogen, wherein
      (a) $R^e$ is
         (1) Ar; or
         (2) a group of the formula

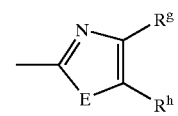

II wherein E is sulfur, oxygen, or N-$R^i$, and $R^g$, $R^h$ and $R^i$ are independently the same as $R^a$, $R^b$ and $R^d$, respectively; or
         (3) a $C_3$–$C_8$ cycloalkyl ring having up to one double bond with the proviso that the carbon linking the cyloalkyl ring to D is saturated, which cycloalkyl ring can be substituted by one or more alkyl-, alkoxycarbonyl-, amino-, aminocarbonyl-, carboxy-, fluoro-, or oxo-substituents; or
         (4) a 5- or 6-membered heteroaryl ring containing at least one and up to three atoms of N for the 6-membered heteroaryl rings and from one to three atoms of N or one atom of O or S and zero to two atoms of N for the 5-membered heteroaryl rings; or (5) hydrogen, (C2–C6)hydroxyalkyl, alkanoylalkyl, alkyl, alkoxycarbonylalkyl, alkenyl, carboxyalkyl (which alkyl can be substituted with alkoxyimino), alkoxycarbonyl, a group $Ar^\Phi$ which is $C_6$- or $C_{10}$- aryl or a 5- or 6-membered, or 9- or 10-membered heteroaryl (wherein the heteroatom is one oxygen, one sulfur or one nitrogen) or $Ar^\Phi$-alkyl; and (b) $R^f$ is independently hydrogen, (C2–C6) hydroxyalkyl, alkanoylalkyl, alkyl, alkoxycarbonylalkyl, alkenyl, carboxyalkyl (which alkyl can be substituted with alkyloxyimino), alkoxycarbonyl, $Ar^\Phi$, or $Ar^\Phi$-alkyl;

wherein aryl, Ar, or $Ar^\Phi$ can be substituted with, in addition to any substitutions specifically noted one or more substituents selected from the group of acylamino, acyloxyalkyl, alkanoyl, alkanoylalkyl, alkenyl, alkoxy, alkoxycarbonyl, alkoxycarbonylalkyl, alkyl, alkylamino, (C1–C3)alkylenedioxy, alkylsulfonyl, alkylsulfinyl, ω-alkylenesulfonic acid, alkylthio, allyl, amino, ArC(O)—, ArC(O)NH—, carboxy, carboxyalkyl, cycloalkyl, dialkylamino, halo, trifluoromethyl, hydroxy, (C2–C6) hydroxyalkyl, mercapto, nitro, ArO—, Ar-, Ar-alkyl-, sulfamoyl, sulfonic acid, 1-pyrrolidinyl, 4-[C6 or C10] arylpiperazin-1-yl-, 4-[C6 or C10]arylpiperidin-1-yl, azetidin-1-yl, morpholin-4-yl, thiomorpholin-4-yl, piperazin-1-yl, piperidin-1-yl; and heterocycles, except those of Ar and $Ar^\Phi$, can be substituted with in addition to any substitutions specifically noted one or more substituents selected from acylamino, alkanoyl, alkoxy, alkoxycarbonyl, alkoxycarbonylalkyl, alkyl, (C1 to C3)alkylenedioxy, alkylamino, alkylsulfonyl, alkylsulfinyl, alkylthio, amino, ArC(O)—, ArO—, Ar-, Ar-alkyl, carboxy, dialkylamino, fluoro, fluoroalkyl, difluoroalkyl, hydroxy, mercapto, oxo, sulfamoyl, trifluoromethyl, 4-[$C_6$ or $C_{10}$]arylpiperidin-1-yl and 4-[$C_6$ or $C_{10}$]arylpiperazin-1-yl;

or a pharmaceutically acceptable salt of said compounds, with the proviso that where the compound of formula I is administered to decrease intraocular pressure at least one compound of formula I administered in effective amount is not a thiazole substituted on a ring carbon with sulfonamide (the amide of which can be substituted) that has carbonic anhydrase inhibiting activity.

For compounds of formula II:

X is nitrogen or sulfur, provided that $R^4$ is present only when X is nitrogen;

the carbon 2 to nitrogen bond is a double bond except when $R^3$ is oxo;

the bond between carbons 4 and 5 is a single bond or a double bond;

$R^1$ and $R^2$ are independently hydrogen, hydroxyalkyl, (C2–C6) alkanoylalkyl, alkyl, alkoxycarbonylalkyl, alkenyl, carboxyalkyl (which alkyl can be substituted with alkyloxyimino), alkoxycarbonyl, a group Ar which is ($C_6$–$C_{10}$) aryl or ($C_5$–$C_9$) heteroaryl (wherein the heteroatom is one oxygen, one sulfur or one nitrogen) or Ar-alkyl, or together with their ring carbons form a $C_6$–$C_{10}$ aromatic fused ring which can be substituted by one or more halo, amino, alkyl, sulfo, or sulfoalkyl, groups, or a $C_1$–$C_3$ alkylenedioxy group, with the proviso that when X is nitrogen $R^1$ and $R^2$ do not form a $C_6$ fused aromatic ring, or together with their ring carbons form a $C_5$–$C_7$ fused cycloalkyl or cycloalkenyl ring having up to two double bonds including a fused double bond of the thiazole radical, which aliphatic ring can be substituted by one or more amino, halo, alkyl, sulfo, sulfoalkyl, carboxy, carboxyalkyl, or oxo groups;

$R^4$ is lower alkyl, lower alkenyl or Ar; and $R^3$ is (a) when X is S, $R^3$ is hydrogen, oxo, alkyl, amino, amino($C_1$–$C_5$)alkyl or aminophenyl, wherein the amino of the latter three groups can be substituted with:

(i) Ar, (ii) Ar-carbonyl, Ar-alkanoyl, Ar-carbonylalkyl, Ar-aminocarbonyl Ar-aminoalkanoyl or Ar-oxyalkanoyl or (iii) formyl or alkanoyl, (b) —NHC(O)(CH$_2$)$_n$—Y—$R^5R^6$, wherein Y is oxygen, sulfur or nitrogen, n is 0 or 1, but n=1 when Y is oxygen or sulfur, and $R^6$ is present only when Y is nitrogen, wherein $R^5$ is (i) Ar; or (ii) a group of the formula

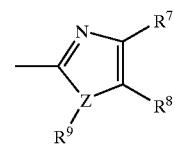

IV wherein $R^7$, $R^8$ and $R^9$ are independently the same as $R^1$, $R^2$ and $R^4$, Z is sulfur or nitrogen, $R^9$ is present only when Z is nitrogen; or (iii) a $C_3$–$C_8$ cycloalkyl or cycloalkenyl ring having up to one double bond, which aliphatic ring can be substituted by one or more amino, halo, alkyl, sulfo, sulfoalkyl, carboxy, carboxyalkyl, or oxo groups; or (iv) a 3 to 8-membered heterocyclic ring wherein the heteroatom is one oxygen, one sulfur or one nitrogen, which heterocyclic ring can be substituted by one or more amino, halo, alkyl, sulfo, sulfoalkyl, carboxy, carboxyalkyl, or oxo groups; or (iv) hydrogen, hydroxyalkyl, (C2–C6)alkanoylalkyl, alkyl, alkoxycarbonylalkyl, alkenyl, carboxyalkyl (which alkyl can be substituted with alkyloxyimino), alkoxycarbonyl, a group Ar which is ($C_6$–$C_{10}$) aryl or ($C_5$–$C_9$) heteroaryl (wherein the heteroatom is one oxygen, one sulfur or one nitrogen) or Ar-alkyl; and $R^6$ is independently hydrogen, hydroxyalkyl, (C2–C6) alkanoylalkyl, alkyl, alkoxycarbonylalkyl, alkenyl, carboxyalkyl (which alkyl can be substituted with alkyloxyimino), alkoxycarbonyl, a group Ar which is (C6–C10) aryl or (C5–C9) heteroaryl (wherein the heteroatom is one oxygen, one sulfur or one nitrogen) or Ar-alkyl;

wherein each group Ar can be substituted by one or more halo, amino, alkyl, alkoxy, alkoxycarbonyl, sulfo, or sulfoalkyl, groups, or a C1–$C_3$ alkylenedioxy group, or a pharmaceutically acceptable salt of said compounds, with the proviso recited above. In this context, "(C2–C6) alkanoylalkyl" identifies the carbon number for the entire substituent.

Arteriosclerosis, Atherosclerosis, Stiff Vessel Disease, Peripheral Vascular Disease, Coronary Stroke Arteriosclerosis is a disease marked by thickening, hardening, and loss of elasticity in arterial walls, of which atherosclerosis is a sub-type. Arteriosclerosis in turn falls within the genus of stiff vessel diseases. Without limitation to theory, it is believed that damage to the blood vessels of these diseases is due to AGE-caused damage, either through protein cross-linking or the stimulation of bioactive agents, or both. Accordingly, the agents are used to treat, prevent, reduce or ameliorate stiff vessel disease, including arteriosclerosis and atherosclerosis. Peripheral vascular disease is an indication that overlaps with atherosclerosis but also covers disease which is believed to have a stronger inflammatory component. First agents are used to treat, prevent, reduce or ameliorate peripheral vascular disease. Coronary heart disease is a form of atherosclerosis of the coronary arteries. First agents are used to treat, prevent, reduce or ameliorate coronary heart disease.

When the heart pumps blood into the vascular system, the ability of the arteries to expand helps to push blood through the body. When arteries become stiff, as they do in the natural process of aging, the ability of the arteries to expand is diminished and also has consequences for the heart. The heart has to work harder to pump the blood into the stiff arteries, and eventually hypertrophies (enlarges in size) to accomplish this. A hypertrophied heart is an inefficient pump, and is one of the disorders that leads to congestive heart failure. One compound believed to work by a mechanism shared by the compounds of the invention showed an ability to reverse the stiffness of arteries in a Phase IIa clinical trial, as measured by the ratio of stroke volume (ml) to pulse pressure (mm Hg). The potential clinical benefit of this is to lessen the effort that the heart must expend to push blood throughout the body. The effect is also believed to contribute to preventing hypertrophy and subsequent inefficiency of the heart, which inefficiency would contribute to congestive heart failure.

Stroke is a cardiovascular disease that occurs when blood vessels supplying blood (oxygen and nutrients) to the brain burst or are obstructed by a blood clot or other particle. Nerve cells in the affected area of the brain die within minutes of oxygen deprivation and loss of nerve cell function is followed by loss of corresponding bodily function. Of the four main types of stroke, two are caused by blood clots or other particles. These two types are the most common forms of stroke, accounting for about 70–80 percent of all strokes.

Blood clots usually form in arteries damaged by atherosclerosis. When plaque tears from the sheer forces of blood flowing over an uneven, rigid cap atop the plaque site, thrombotic processes become involved at the "injury" site. As a result, clots can form. First agents are used to prevent, reduce or ameliorate the risk of stroke in patients who have suffered previous strokes or have otherwise been identified as at risk.

First agents can also be used to treat, prevent, reduce or ameliorate peripheral vascular disease and periarticular rigidity.

Atherosclerosis is a disease that involves deposition of blood lipids in plaque in the arteries throughout the body. In coronary arteries, accumulation of plaque progressively leads to reduced coronary flow, with occlusion of the arteries causing focal death of cardiac tissue (myocardial infarction, heart attack). If the amount of tissue that dies is large enough, death ensues. In a Phase IIa trial, one compound believed to work by a mechanism shared by the compounds of the invention increased the amount of circulating triglycerides (lipids). Consistent with the known presence of AGEs in plaque, the result indicates that the agent had a lipid mobilizing effect on arterial plaque. Reducing local deposits of plaque should eventually lessen the risk of myocardial infarction and death due to heart attacks.

Rheumatoid Arthritis, Osteoarthritis, Bone Resorption

It is believed, without limitation to such theory, that reducing AGE accumulation at the joints affected by rheumatoid arthritis or osteoarthritis reduces stimulation of the production of cytokines involved in inflammatory processes of the disease. Treatment using the invention is expected to treat, prevent, reduce or ameliorate rheumatoid arthritis or osteoarthritis. Similarly, it is believed that reducing AGE accumulation at bone reduces stimulation of bone resorption. Accordingly, the invention is used to treat, prevent, reduce or ameliorate osteoporosis, bone loss or brittle bone.

Dialysis

The agents can be administered as part of a dialysis exchange fluid, thereby preventing, limiting or ameliorating the damage to tissue caused by the sugars found in such exchange fluid. For example, agents are expected to prevent, limit or ameliorate the stiffening and sclerosing of peritoneal tissue that occurs in peritoneal dialysis, as well as prevent, limit or ameliorate the formation of new blood vessels in the peritoneal membrane. In hemodialysis, agents are expected to prevent, limit or ameliorate the stiffening and sclerosing of red blood cells and vasculature resulting from exposure to the sugars exchanged into the blood during dialysis. Exchange fluids for peritoneal dialysis typically contain 10–45 g/L of reducing sugar, typically 25 g/L, which causes the formation of AGEs and consequent stiffening and degradation of peritoneal tissue. Similarly, hemodialysis fluids typically contain up to about 2.7 g/L of reducing sugar, typically 1 to 1.8 g/L. Thus, the invention provides methods by which the agents are provided in these fluids and thereby prevent, limit or ameliorate the damage that would otherwise result. Alternatively, the invention provides methods whereby the agents are administered by the methods described below to prevent, limit or ameliorate such damage from dialysis. In hemodialysis, the exchange fluid preferably contains 0.006–2.3 mg/L of an agent of the invention, more preferably, 0.06 to 1.0 mg/L. In peritoneal dialysis, the exchange fluid preferably contains 0.01 to 24 mg/L of an agent of the invention, or preferably, 1.0 to 10 mg/L.

In one embodiment, preventing or ameliorating is effected with a second agent, which is a compound of the aminoguanidine class as described below. A preferred route of administration is inclusion in the dialysis fluids. In hemodialysis, the exchange fluid preferably contains 0.125 to 2.5 mg/L of aminoguanidine, more preferably, 0.2 to 1.0 mg/L. In peritoneal dialysis, the exchange fluid preferably contains 1.25 to 25 mg/L of aminoguanidine, or preferably, 2.0 to 10 mg/L. In a preferred aspect of the invention, the agents are initially administered, and subsequently second agents are used to moderate or limit damage thereafter.

Sickle Cell Anemia

It is believed, without limitation to such theory, that the agents act to prevent, reduce or ameliorate the restraint on blood flow caused by sickling. Again without limitation to theory, the mode of action is believed to be in reducing vascular as well as blood cell inelasticity. Accordingly, the agents are used to treat, prevent, reduce or ameliorate sickle cell anemia.

End Stage Renal Disease, Diabetic Nephropathy

Diabetic Nephropathy is a complication of diabetes that evolves early, typically before clinical diagnosis of diabetes is made. The earliest clinical evidence of nephropathy is the appearance of low but abnormal levels (>30 mg/day or 20 μg/min) of albumin in the urine (microalbuminuria), followed by albuminuria (>300 mg/24 h or ~200 μg/min) that develops over a period of 10–15 years. In patients with type 1 diabetes, diabetic hypertension typically becomes manifest early on, by the time that patients develop microalbuminuria. Once overt nephropathy occurs, the glomerular filtration rate (GFR) falls over several years resulting in End Stage Renal Disease (ESRD) in 50% of type 1 diabetic individuals within 10 years and in >75% of type 1 diabetics by 20 years of onset of overt nephropathy. Albiminuria (i.e., proteinuria) is a marker of greatly increased cardiovascular morbidity and mortality for patients with either type 1 or type 2 diabetes.

Without limitation to theory, it is believed that damage to the glomeruli and blood vessels of the kidney is due to AGE-caused damage, either through protein cross-linking or the stimulation of bioactive agents, or both. Accordingly, the agents are used to treat, prevent, reduce or ameliorate damage to kidney in patients at risk for ESRD. The agents can also be used to treat, prevent, reduce or ameliorate glomerulosclerosis.

Hypertension, Isolated Systolic Hypertension

Cardiovascular risk correlates more closely with the systolic and the pulse pressure than with the diastolic pressure. In diabetic patients, the cardiovascular risk profile of diabetic patients is strongly correlated to duration of diabetes, glycemic control and blood pressure. Structural matrix proteins contribute to the function of vessels and the heart, and changes in the physical behavior of cardiovascular walls are believed to be important determinants of circulatory function. In elderly individuals, the loss of compliance in the aorta leads to isolated systolic hypertension, which in turn expands the arterial wall and thereby diminishes the dynamic range of elasticity. In vivo studies in rodents, canines and in primates indicate potential utility of a compound believed to operate by the AGE-mediated mechanism in substantially ameliorating vascular stiffening. For example, in a dog model for diabetes, lower end diastolic pressure and increased end diastolic volume, indicators of ventricular elasticity, returned to a value at about the midpoint between the disease impaired value and the value for control dogs. Treatment with the shared-mechanism compound lead to a reduction in the mass of collagen in cardiovascular tissues. In situ hybridization studies demonstrate that the compound reduces the expression of both Type IV collagen and TGFbeta.

Compared with that of a non-diabetic, the diabetic artery is smaller as it is stiffer. As in isolated systolic hypertension in which vessels stiffen with age and lose the dynamic range of expansion under systole. First agents are used to treat, prevent, reduce or ameliorate hypertension, including isolated systolic hypertension and diabetic hypertension. Moreover, the same benefit is anticipated for the more rare hypertensive disorder, pulmonary hypertension. Pulmonary hypertension is a rare blood vessel disorder of the lung in which the pressure in the pulmonary artery (the blood vessel that leads from the heart to the lungs) rises above normal levels and may become life threatening. The similarity in development of elevated blood pressure in the pulmonary bed with the increase in systemic blood pressure in diabetic hypertension and in isolated systolic hypertension suggests similar mechanisms are involved.

Pulse pressure is the difference between systolic and diastolic blood pressure. In a young human, systolic pressure is typically 120 mm Hg and diastolic pressure is 80 mm Hg, resulting in a pulse pressure of 40 mm Hg. With age, in many individuals pulse pressure increases, largely due to the increase in systolic pressure that results from stiff vessel disease. In individuals with pulse pressure greater than 60 mm Hg there is an increased risk of death from cardiovascular morbidities. In a Phase IIa trial, one compound believed to work by a mechanism shared by the compounds of the invention reduced pulse pressure in elderly patients with pulse pressures greater than 60 mm Hg in a statistically significant manner. This decrease in pulse pressure was believed to be due primarily to the effect of the agent on lowering the systolic blood pressure.

The agents of the invention are used to treat, prevent, reduce or ameliorate reduced vascular compliance, elevated pulse pressure, and hypertension. Moreover, the agents are used to reduce pulse pressure, increase vascular compliance, or decrease the risk of death.

Heart Failure

Congestive Heart Failure (CHF) is a clinical syndrome that entails cardiac disease of the ventricle. Diastolic dysfunction is a subset of heart failure in which the left ventricle stiffens with age. The stiffening of the left ventricle that occurs in CHF and in diastolic dysfunction is believed to result from increased crosslinking of collagen fibers with age and/or fibrosis and related hypertrophy. First agents are used to treat, prevent, reduce or ameliorate heart failure.

Retinopathy

The effect of diabetes on the eye is called diabetic retinopathy and involves changes to the circulatory system of the retina. The earliest phase of the disease is known as background diabetic retinopathy wherein the arteries in the retina become weakened and leak, forming small, dot-like hemorrhages. These leaking vessels often lead to swelling or edema in the retina and decreased vision. The next stage is proliferative diabetic retinopathy, in which circulation problems cause areas of the retina to become oxygen-deprived or ischemic. New vessels develop as the circulatory system attempts to maintain adequate oxygen levels within the retina. Unfortunately, these new vessels hemorrhage easily. In the later phases of the disease, continued abnormal vessel growth and scar tissue may cause serious problems such as retinal detachment and glaucoma. First agents are used to treat, prevent, reduce or ameliorate diabetic retinopathy. The agents can be administered by the methods described below, including by topical administration to the eye. The agents can also be administered by intravitreal implant.

Cataracts, Other Damage to Lens Proteins

AGE-mediated crosslinking and/or fibrotic processes are believed to contribute to cataract formation and formation of other damage to lens proteins. First agents are used to treat, prevent, reduce or ameliorate cataracts or other damage to lens proteins.

Alzheimer's Disease

Considerable evidence exists implicating AGEs that form in the neurofibrillary tangles (tau protein) and senile plaques (beta-amyloid peptide) in early neurotoxic processes of Alzheimer's disease. Insoluble human tau protein is likely crosslinked. Glycation of insoluble tau from AD patients and experimentally AGE-modified tau generate oxygen free radicals, resulting in the activation of transcription via nuclear factor-kappa B, and resulting in an increase in amyloid beta-protein precursor and release of amyloid beta-peptides. Thus, A.G.E.-modified tau may function as an initiator in a positive feedback loop involving oxidative stress and cytokine gene expression. First agents are used to treat, prevent, reduce or ameliorate Alzheimer's disease.

Other Indications

For reasons analogous to those set forth above, the invention is believed to be useful in treating, preventing, reducing or ameliorating diabetes or its associated adverse sequelae, and peripheral neuropathy. The agents, especially in topical form, increase elasticity and/or reduce wrinkles in skin. The agents further increase red blood cell deformability.

Combination Therapies

For all indications, agents can be administered concurrently or in a combined formulation with aminoguanidine or other agents of the aminoguanidine class, which are administered in effective amounts as is known in the art. These agents are preferably administered separately from the other compounds described herein. These agents include compounds of formula A

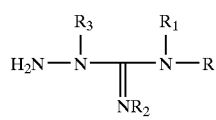

(A)

wherein R is an alkyl group, or a group of the formula —N(R⁴)(R⁵) wherein R⁴ is hydrogen, and R⁵ is an alkyl group or a hydroxyalkyl group; or R⁴ and R⁵ together with the nitrogen atom are a heterocyclic group containing 4–6 carbon atoms and, in addition to the nitrogen atom, 0–1 oxygen, nitrogen or sulfur atoms; R¹ is hydrogen or an amino group; R² is hydrogen or an amino group; R³ is hydrogen or an alkyl group, wherein R and R¹ cannot both be amino groups. Preferably at least one of R¹, R², and R³ is other than hydrogen. The compounds can be used as their pharmaceutically acceptable acid addition salts, and mixtures of such compounds. When aminoguanidine compounds are administered, they can be administered by any route of pharmaceutical administration including those discussed below for other first agents.

The method of the invention is used to treat animals, preferably mammals, preferably humans.

In accordance with the present invention, methods for administering pharmaceutical compositions containing compounds have been developed for the treating the indications of the invention. These agents are either substituted thiazole, oxazole, or imidazole agents as shown in the Summary section above.

As is noted in the formula for I, IA and III, the invention includes aromatic thiazole, oxazole, and imidazole analogs, as well as non aromatic analogs thereof such as thiazoline, thiazolidine, oxazoline, oxazolidine, imidazoline, and imidazolidine analogs.

The alkyl, and alkenyl groups referred to above include both C1 to C6 linear and branched alkyl and alkenyl groups, unless otherwise noted. Alkoxy groups include linear or branched C1 to C6 alkoxy groups, unless otherwise noted. The size range for carbon-containing substituents that by definition need a minimum of two carbons, or which need a minimum number of carbons for stability, will be recognized to start from the appropriate size. These groups are optionally substituted by one or more halo, hydroxy, amino or lower alkylamino groups.

"Ar" (consistent with the rules governing aromaticity) refers to a $C_6$ or $C_{10}$ aryl, or a 5 or 6 membered heteroaryl ring. The heteroaryl ring contains at least one and up to three atoms of N for the 6 membered heteroaryl ring. The 5 membered heteroaryl ring contains; (1) from one to three atoms of N, or (2) one atom of O or S and zero to two atoms of N. Nonlimiting examples of heteroaryl groups include: pyrrolyl, furanyl, thienyl, pyridyl, oxazolyl, pyrazolyl, pyrimidinyl, and pyridazinyl.

"Ar" can be fused to either a benzene, pyridine, pyrimidine, pyridazine, or (1,2,3) triazine ring. As used herein, $C_6$ or $C_{10}$ aryl groups and heteroaryl containing five or six, or nine to ten ring members are monocyclic or bicyclic.

In certain embodiments of the invention, the thiazoles, imidazoles, and oxazoles of the invention contain $R^a$ and $R^b$ substitutions that together with their ring carbons (the C4–C5 carbons of the thiazoles, imidazoles, and oxazoles) form a five to eight membered fused heterocycle (i.e. a bicyclic heterocycle is formed). In these embodiments the fused heterocycle is preferably not aromatic. Particular compounds within these embodiments contain sulfur atoms in the fused heterocycle (the ring fused to the thiazoles, imidazoles, and oxazoles). These sulfur atoms in these particular compounds can exist in various oxidation states, as $S(O)_n$, where n is 0, 1, or 2.

In certain embodiments of the invention, thiazoles, imidazoles, and oxazoles of the invention contain $R^a$ and $R^b$ substitutions that together with their ring carbons (the C4–C5 carbons of the thiazoles, imidazoles, and oxazoles) form a C5 to C7 cycloalkyl ring having up to two double bonds including the C4–C5 double bond. In other embodiments a cycloalkyl ring is present when $R^e$ is a C3 to C8 cycloalkyl ring. The cycloalkyl groups can be substituted by one or more of the group consisting of alkyl-, alkoxycarbonyl-, amino-, aminocarbonyl-, carboxy-, fluoro-, or oxo- substituents. One of ordinary skill in the art will recognize that where cycloalkyl groups contain double bonds, the sp² hybridized carbon atoms can contain only one substituent (which cannot be amino- or oxo-). Sp³ hybridized carbon atoms in the cycloalkyl ring can be geminally substituted with the exception that (1) two amino groups and (2) one amino and one fluoro group can not be substituted on the same sp³ hybridized carbon atom.

In certain embodiments of the invention, the thiazoles, imidazoles, and oxazoles of the invention contain $R^a$ and $R^b$ substitutions that together with their ring carbons (the C4–C5 carbons of the thiazoles, imidazoles, and oxazoles) form a five or six membered heteroaryl ring (i.e, a bicyclic aromatic heterocycle is formed). A preferred bicyclic aromatic heterocycle of the invention is a purine analog [J is N—$R^d$ and $R^a$ and $R^b$ together with their ring carbons (the C4 and C5 of the imidazole ring) form a pyrimidine ring].

Aryl, Ar, or Ar$^\Phi$ can be substituted with, in addition to any substitutions specifically noted one or more substituents selected from the group of acylamino, acyloxyalkyl, alkanoyl, alkanoylalkyl, alkenyl, alkoxy, alkoxycarbonyl, alkoxycarbonylalkyl, alkyl, alkylamino, (C1–C3) alkylenedioxy, alkylsulfonyl [alkylSO₂—], alkylsulfinyl [alkylSO—], ω-alkylenesulfonic acid [—(CH₂)ₙSO₃H where n=1 to 6], alkylthio, allyl, amino, ArC(O)—, ArC(O)NH—, carboxy, carboxyalkyl, cycloalkyl, dialkylamino, halo, trifluoromethyl, hydroxy, (C2-C6)hydroxyalkyl, mercapto, nitro, ArO—, Ar-, Ar-alkyl-, sulfamoyl, sulfonic acid, morpholin-4-yl, thiomorpholin-4-yl, piperidin-1-yl, 1-pyrrolidinyl, 4-[$C_6$ or $C_{10}$]arylpiperidin-1-yl and 4-[$C_6$ or $C_{10}$]arylpiperazin-1-yl.

Heterocycles, except those of Ar and Ar$^\Phi$, can be substituted with in addition to any substitutions specifically noted one or more substituents selected from acylamino, alkanoyl, alkoxy, alkoxycarbonyl, alkoxycarbonylalkyl, alkyl, (C1 to C3)alkylenedioxy, alkylamino, alkylsulfonyl, alkylsulfinyl, alkylthio, amino, ArC(O)—, ArO—, Ar-, Ar-alkyl, carboxy, dialkylamino, fluoro, fluoroalkyl, difluoroalkyl, hydroxy, mercapto, oxo, sulfamoyl, trifluoromethyl, 4-[$C_6$ or $C_{10}$]arylpiperidin-1-yl and 4-[$C_6$ or $C_{10}$]arylpiperazin-1-yl, wherein multiple substituents are located on different atoms of the heterocyclic ring, with the proviso that alkyl, alkoxycarbonyl, and fluoro substituents can be substituted on the same carbon atom of the heterocyclic ring. Heterocycles can be substituted with one or more substituents.

The halo atoms can be fluoro, chloro, bromo or iodo. Chloro and fluoro are preferred for aryl substitutions.

In certain embodiments, such compounds are not
(1) 5-methylthiazole,
(2) benzothiazole, or
(3) 2,6-diamino-benzothiazole.

The method can comprise administering an amount effective therefor of one or more compounds of the following formula:

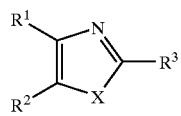

II

The method can also comprise administering an amount effective therefor of one or more compounds of the following formula:

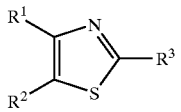

III

The method can also comprise administering an amount effective therefor of one or more compounds of formula I, wherein each Ar or cycloalkyl group is substituted with up to two substituents.

In some embodiments of this invention, the compounds of formula I, IA and III can form biologically and pharmaceutically acceptable salts. Useful salt forms include the halides, particularly the bromide, chloride, tosylate, methanesulfonate, brosylate, fumarate, maleate, succinate, acetate, mesitylenesulfonate and the like. Other related salts can be formed using similarly non-toxic, biologically or pharmaceutically acceptable anions.

Representative, non-limiting examples of compounds of the present invention are:
Thiazole
4,5-Dimethylthiazole
4-Methylthiazole
5-Methylthiazole
4-Methyl-5-(2-hydroxyethyl)thiazole
4-Methyl-5-vinylthiazole
Benzothiazole
2-Aminobenzothiazole
2-Amino-4-chlorobenzothiazole
2-Amino-6-chlorobenzothiazole
2,6-Diamino-benzothiazole
2-Aminothiazole
2,4,5-Trimethylthiazole
2-Amino-5-methylthiazole
2-Amino-4-methylthiazole
2-Acetylthiazole
2-Ethyl-4-methylthiazole
Ethyl 2-(Formylamino)-4-thiazoleacetate
2-(Formylamino)-alpha-(methoxyimino)-4-thiazoleacetic acid
2-Amino-4-phenylthiazole hydrochloride monohydrate
2-Isobutylthiazole
2-Methyl-2-thiazoline
2-Methyl-2-oxazoline
2-Oxazolidone
2-Amino-4-thiazoleacetic acid
1-(Thiazolyl)-3-phenyl-urea
1-(Thiazolidinyl)-3-(4-fluorophenyl)-urea
(4-fluorophenyl)thiazolin-2-ylamine
2-(4,6-dimethylpyrimidin-2-ylthio)-N-(1,3-thiazol-2'yl)acetamide, also known as
N-(Thiazolyl)-2-(4,6-dimethyl-pyrimidin-2-yl-thio)-acetamide

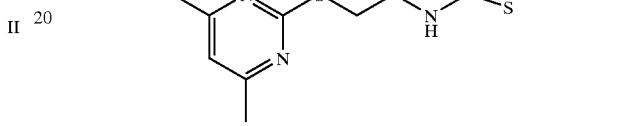

2-(4-propylphenoxy)-N-(thiazol-2-yl)acetamide
2-furyl-N-[4-(6-methylbenzothiazol-2-yl)phenyl]carboxamide
2-(3,5-Dimethylphenoxy)-N-thiazol-2-yl)acetamide
5,5-Dimethyl-2-(2-naphthylamino)-4,5,6-trihydrolbenzothiazol-7-one
Imidazole
1-Methylimidazole
1-Ethylimidazole
1-Butylimidazole
1-Vinyliidazole
1-Allylimidazole
1-(Trimethylsilyl)imidazole
1-(3-Aminopropyl)imidazole
1-Benzyl imidazole
1-Phenyl imidazole
1,5-Dicyclohexyl imidazole
1-(p-Toluenesulfonyl)imidazole
N-Benzoyl-imidazole
4-Methyl-imidazole
4'-(Imidazol-1-yl)-acetophenone
4-(Imidazol-1-yl)-phenol
1-(4-Methoxyphenyl)-1H-imidazole
Methyl-4-(1H-imidazol-1yl)benzoate
1-Methylbenzimidazole
2-(3,5-dimethylphenoxy)-N-(4-methyl(1,3-thiazol-2-yl))acetamide
2-(3,5-dimethylphenoxy)-N-(5-methyl(1,3-thiazol-2-yl))acetamide
N-(4,5-dimethyl(1,3-thiazol-2-yl))-2-(3,5-dimethylphenoxy)acetamide
2-(3,5-dimethylphenoxy)-N-[5-(2-hydroxyethyl)-4-methyl(1,3-thiazol-2-yl)]acetamide
2-(3,5-dimethylphenoxy)-N-(5-chloro(1,3-thiazol-2-yl))acetamide
N-benzothiazol-2-yl-2-(3,5-dimethylphenoxy)acetamide
2-(3,5-dimethylphenoxy)-N-(5-bromo(1,3-thiazol-2-yl))acetamide
2-(3,5-dimethylphenoxy)-N-(4-phenyl(1,3-thiazol-2-yl))acetamide
ethyl 2-[2-(3,5-dimethylphenoxy)acetylamino]-4-phenyl-1,3-thiazole-5-carboxylate 2-(3,5-dimethylphenoxy)-N-(5-nitro(1,3-thiazol-2-yl)) acetamide
2-(3,5-dimethylphenoxy)-N-(6-nitrobenzothiazol-2-yl) acetamide
ethyl 2-[2-(3,5-dimethylphenoxy)acetylamino]-1,3-thiazole-4-carboxylate
2-(3,5-dimethylphenoxy)-N-(1-methylimidazol-2-yl) acetamide
2-(3,5-dimethylphenoxy)-N-(1-methylbenzimidazol-2-yl) acetamide
2-(3,5-dimethylphenoxy)-N-[1-benzylbenzimidazol-2-yl] acetamide
2-(3,5-dimethylphenoxy)-N-(5-chlorobenzoxazol-2-yl) acetamide as well as other biologically and pharmaceutically acceptable salts thereof.

Certain of the compounds of the invention are novel compounds which represent a further embodiment of the present invention. These compounds are represented, for example, by the compounds of formula I, IA or III where $R^c$ or $R^3$ is —NHC(O)(CH$_2$)$_n$-D-R$^e$R$^f$ or —NHC(O)(CH$_2$)$_n$—Y—R$^5$R$^6$. In one embodiment, these are compounds where n=1. In another embodiment, these are compounds where Y or D is oxygen or sulfur. In another embodiment, preferably where Y or D is oxygen or sulfur, (a) $R^e$ is
  (1) Ar,
  (2) a group of the formula

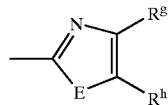

II wherein E is sulfur, oxygen, or N—$R^i$, and $R^g$, $R^h$ and $R^i$ are independently the same as $R^a$, $R^b$ and $R^d$, respectively, (3) a $C_3$–$C_8$ cycloalkyl ring having up to one double bond with the proviso that the carbon linking the cyloalkyl ring to D is saturated, which cycloalkyl ring can be substituted by one or more alkyl-, alkoxycarbonyl-, amino-, aminocarbonyl-, carboxy-, fluoro-, or oxo-substituents; or (4) a 5- or 6-membered heteroaryl ring containing at least one and up to three atoms of N for the 6-membered heteroaryl rings and from one to three atoms of N or one atom of O or S and zero to two atoms of N for the 5-membered heteroaryl rings;

Or,
wherein $R^5$ is
  (i) Ar,
  (ii) a group of the formula

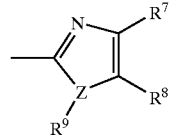

IV wherein $R^7$, $R^8$ and $R^9$ are independently the same as $R^1$, $R^2$ and $R^4$, Z is sulfur or nitrogen, $R^9$ is present only when Z is nitrogen;

(iii) a $C_3$–$C_8$ cycloalkyl or cycloalkenyl ring having up to one double bond, which aliphatic ring can be substituted by one or more amino, halo, alkyl, sulfo, sulfoalkyl, carboxy, carboxyalkyl, or oxo groups; or (iv) a 3 to 8-membered heterocyclic ring wherein the heteroatom is one oxygen, one sulfur or one nitrogen, which heterocyclic ring can be substituted by one or more amino, halo, alkyl, sulfo, sulfoalkyl, carboxy, carboxyalkyl, or oxo groups.

The above compounds where $R^c$ or $R^3$ is —NHC(O)(CH$_2$)$_n$—D—R$^3$R$^f$ or —NHC(O)(CH$_2$)$_n$—Y—R$^5$R$^6$ are those wherein at least one of $R^a$ and $R^b$, or $R^1$ and $R^2$ is other than hydrogen.

In one embodiment, the compound is according to Formula I or IA and $R^c$ is dialkylamino(C$_1$–C$_5$)alkyl. In this embodiment, preferably, J is sulfur.

Useful intermediates include a compound consistent with Formula I or IA, where $R^c$ is ω-halo(C$_2$–C$_5$)alkyl. In this embodiment, preferably, J is sulfur.

Further provided are compounds of formula I or IA,

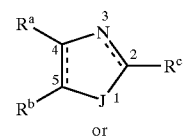

I or

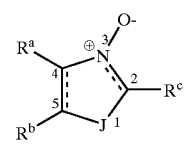

IA wherein:
a. J is sulfur;
b. $R^a$ is hydroxyalkyl or alkyl omega-substituted with a tertiary amine which is dialkyl amine or (i) incorporated into a 5- or 6-membered heteroaryl ring, wherein the 6- membered heteroaryl ring contains one to three atoms of N, and the 5-membered heteroaryl ring contains from one to three atoms of N or one atom of O or S and one to two atoms of N or (ii) incorporated into a 5- or 6-membered non-aromatic heterocyclic ring having one to two ring nitrogens; and
c. $R^b$ and $R^c$ are alkyl. These compounds can be used in the methods of the invention.

Also provided are compounds of formula I or IA,

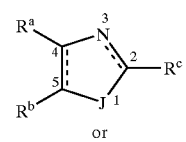

I or

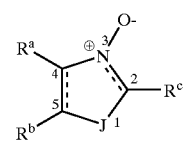

IA wherein:
a. J is sulfur;
b. the carbon 2 to nitrogen bond is a double bond;
c. the bond between carbons 4 and 5 is a double bond;
d. $R^a$ and $R^b$ are independently selected from hydrogen, acylamino, alkanoyl, alkanoylalkyl, alkoxy, alkoxycarbonyl, alkoxycarbonylalkyl, alkyl, (C2–C6)

hydroxyalkyl, nitro, trifluoromethyl, Ar {wherein, Ar is $C_6$ or $C_{10}$ aryl}, or Ar-alkyl; and c. $R^c$ is alkyl omega-substituted with a tertiary amine which is dialkyl amine or (i) incorporated into a 5- or 6-membered heteroaryl ring, wherein the 6-membered heteroaryl ring contains one to three atoms of N, and the 5-membered heteroaryl ring contains from one to three atoms of N or one atom of O or S and one to two atoms of N or (ii) incorporated into a 5- or 6-membered non-aromatic heterocyclic ring having one to two ring nitrogens, wherein aryl can be substituted with one or more substituents selected from the group of acylamino, acyloxyalkyl, alkanoyl, alkanoylalkyl, alkenyl, alkoxy, alkoxycarbonyl, alkoxycarbonylalkyl, alkyl, (C1–C3) alkylenedioxy, alkylthio, allyl, carboxyalkyl, cycloalkyl, dialkylamino, halo, trifluoromethyl, hydroxy, (C2–C6)hydroxyalkyl, mercapto, nitro, ArO—, Ar-, or Ar-alkyl-.

These compounds can be used in the methods of the invention.

Further provided are compounds of formula I or IA,

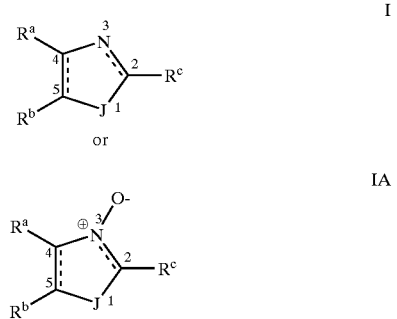

wherein:
a. J is sulfur;
b. the carbon 2 to nitrogen bond is a double bond;
c. the bond between carbons 4 and 5 is a double bond;
d. $R^a$ and $R^b$ are independently selected from hydrogen, acylamino, alkanoyl, alkanoylalkyl, alkoxy, alkoxycarbonyl, alkoxycarbonylalkyl, alkyl, (C2–C6) hydroxyalkyl, nitro, trifluoromethyl, Ar {wherein, Ar is $C_6$ or $C_{10}$ aryl}, or Ar-alkyl;
e. $R^c$ is ($C_2$–$C_5$)alkyl omega-substituted with halo, wherein aryl can be substituted with one or more substituents selected from the group of acylamino, acyloxyalkyl, alkanoyl, alkanoylalkyl, alkenyl, alkoxy, alkoxycarbonyl, alkoxycarbonylalkyl, alkyl, (C1–C3) alkylenedioxy, alkylthio, allyl, carboxyalkyl, cycloalkyl, dialkylamino, halo, trifluoromethyl, hydroxy, (C2–C6)hydroxyalkyl, mercapto, nitro, ArO—, Ar-, or Ar-alkyl-.

The compounds of the invention are capable of inhibiting the formation of advanced glycosylation endproducts on target molecules, including, for instance, proteins, as well as being capable of breaking or reversing already formed advanced glycosylation endproducts on such proteins. The cross-linking of protein by formation of advanced glycosylation endproducts contributes to the entrapment of other proteins and results in the development in vivo of conditions such as reduced elasticity and wrinkling of the skin, certain kidney diseases, atherosclerosis, osteoarthritis and the like. Similarly, plant material that undergoes nonenzymatic browning deteriorates and, in the case of foodstuffs, become spoiled or toughened and, consequently, inedible, unpalatable or non-nutritious. Thus, the compounds employed in accordance with this invention inhibit this late-stage Maillard effect and intervene in the deleterious changes described above, and reduce the level of the advanced glycosylation endproducts already present in the protein material.

A rationale of the present invention is to use agents which block, as well as reverse, the post-glycosylation step, e.g., the formation of fluorescent chromophores and cross-links, the presence of which is associated with, and leads to adverse sequelae of diabetes and aging. An ideal agent would prevent the formation of such chromophores and of cross-links between protein strands and trapping of proteins onto other proteins, such as occurs in arteries and in the kidney, and reverse the level of such cross-link formation already present.

The chemical nature of the early glycosylation products with which the compounds of the present invention are believed to react can vary. Accordingly the term "early glycosylation product(s)" as used herein is intended to include any and all such variations within its scope. For example, early glycosylation products with carbonyl moieties that are involved in the formation of advanced glycosylation endproducts, and that can be blocked by reaction with the compounds of the present invention, have been postulated. In one embodiment, the early glycosylation product can comprise the reactive carbonyl moieties of Amadori products or their further condensation, dehydration and/or rearrangement products, which can condense to form advanced glycosylation endproducts. In another scenario, reactive carbonyl compounds, containing one or more carbonyl moieties (such as glycolaldehyde, glyceraldehyde or 3-deoxyglucosone) can form from the cleavage of Amadori or other early glycosylation endproducts, and by subsequent reactions with an amine or Amadori product, can form carbonyl containing advanced glycosylation products such as alkylformyl-glycosylpyrroles.

While not wishing to be bound by any particular theory as to the mechanism by which the compounds of the instant invention reverse already formed advanced glycosylation endproducts, studies have been structured to elucidate a possible mechanism. Earlier studies examining the fate of the Amadori product (AP) in vivo have identified one likely route that could lead to the formation of covalent, glucose-derived protein crosslinks. This pathway proceeds by dehydration of the AP via successive beta-eliminations as shown in the Scheme A of U.S. Pat. No. 5,853,703. Thus, loss of the 4-hydroxyl of the AP (1) gives a 1,4-dideoxy-1-alkylamino-2,3-hexodiulose (AP-dione) (2). An AP-dione with the structure of an amino-1,4-dideoxyosone has been isolated by trapping model APs with the AGE-inhibitor aminoguanidine. Subsequent elimination of the 5-hydroxyl gives a 1,4,5-trideoxy-1-alkylamino-2,3-hexulos-4-ene (AP-ene-dione) (3), which has been isolated as a triacetyl derivative of its 1,2-enol form. Amadoridiones, particularly the AP-ene-dione, would be expected to be highly reactive toward protein crosslinking reactions by serving as targets for the addition of the amine (Lys, His)-, or sulfhydryl (Cys)-based nucleophiles that exist in proteins, thereby producing stable crosslinks of the form (4). Note that the linear AP-ene-dione of (3) and the stable cross-link of (4) can cyclize to form either 5- or 6-member lactol rings. See, the scheme shown in U.S. Pat. No. 5,853,703.

The possibility that a major pathway of glucose-derived crosslink formation proceeds through an AP-ene-dione intermediate was investigated by experiments designed to test the occurrence of this pathway in vivo as well as to effect the specific cleavage of the resultant α-dicarbonyl-based protein crosslinks. Without being limited to theory, at least some of the compounds of the invention are believed to act as "bidentate" nucleophiles, particularly designed to effect a carbon-carbon breaking reaction between the two carbonyls of the crosslink, in a similar manner to Scheme B of U.S. Pat. No. 5,853,703.

Therapeutic implications of the present invention relate to the arrest, and to some extent, the reversal of the aging process which has, as indicated earlier, been identified and exemplified in the aging of key proteins by advanced glycosylation and cross-linking. Thus, body proteins, and particularly structural body proteins, such as collagen, elastin, lens proteins, nerve proteins, kidney glomerular basement membranes and other extravascular matrix components would all benefit in their longevity and operation from the practice of the present invention. The present invention thus reduces the incidence of pathologies involving the entrapment of proteins by cross-linked target proteins, such as retinopathy, cataracts, diabetic kidney disease, glomerulosclerosis, peripheral vascular disease, arteriosclerosis obliterans, peripheral neuropathy, stroke, hypertension, atherosclerosis, osteoarthritis, periarticular rigidity, loss of elasticity and wrinkling of skin, stiffening of joints, glomerulonephritis and the like. Likewise, all of these conditions are in evidence and tend to occur at an accelerated rate in patients afflicted with diabetes mellitus as a consequence of this hyperglycemia. Thus, the present therapeutic method is relevant to treatment of these and related conditions in patients either of advanced age or those suffering from one of the mentioned pathologies.

Protein cross-linking through advanced glycosylation product formation can decrease solubility of structural proteins such as collagen in vessel walls and can also trap serum proteins, such as lipoproteins to the collagen. Also, this can result in increased permeability of the endothelium and consequently covalent trapping of extravasated plasma proteins in subendothelial matrix, and reduction in susceptibility of both plasma and matrix proteins to physiologic degradation by enzymes. For these reasons, the progressive occlusion of diabetic vessels induced by chronic hyperglycemia is believed to result from excessive formation of glucose-derived cross-links. Such diabetic microvascular changes and microvascular occlusion can be effectively prevented and reversed by chemical inhibition and reversal of the advanced glycosylation product formation utilizing a composition and the methods of the present invention.

Molecular cross-linking through advanced glycosylation product formation can decrease solubility of structural proteins such as collagen in vessel walls and can also trap serum proteins, such as lipoproteins to the collagen. Also, this can result in increased permeability of the endothelium and consequently covalent trapping of extravasated plasma proteins in subendothelial matrix, and reduction in susceptibility of both plasma and matrix proteins to physiologic degradation by enzymes. For these reasons, the progressive occlusion of diabetic vessels induced by chronic hyperglycemia has been hypothesized to result from excessive formation of sugar-derived and particularly, glucose-derived cross-links. Such diabetic microvascular changes and microvascular occlusion can be effectively prevented and reversed by chemical inhibition and reversal of the advanced glycosylation product formation utilizing a composition and the methods of the present invention.

Studies indicate that the development of chronic diabetic damage in target organs is primarily linked to hyperglycemia so that tight metabolic control would delay or even prevent end-organ damage. See Nicholls et al., Lab. Invest., 60, No. 4, p. 486 (1989), which discusses the effects of islet isografting and aminoguanidine in murine diabetic nephropathy. These studies further evidence that aminoguanidine diminishes aortic wall protein cross-linking in diabetic rats and confirm earlier studies by Brownlee et al., Science, 232:1629–1632 (1986) to this additional target organ of complication of diabetes. Also, an additional study showed the reduction of immunoglobulin trapping in the kidney by aminoguanidine (Brownlee et al., Diabetes, (1):42A (1986)).

Further evidence in the streptozotocin-diabetic rat model that aminoguanidine administration intervenes in the development of diabetic nephropathy was presented by Brownlee et al., Science, 232:1629–1632 (1986), with regard to morphologic changes in the kidney which are hallmarks of diabetic renal disease. These investigators reported that the increased glomerular basement membrane thickness, a major structural abnormality characteristic of diabetic renal disease, was prevented with aminoguanidine.

Taken together, these data strongly suggest that inhibition and reversal of the formation of advanced glycosylation endproducts (AGEs), by the teaching of the present invention, can prevent, as well as to some extent reverse late, as well as early, structural lesions due to diabetes, as well as changes during aging caused by the formation of AGEs.

Diabetes-induced changes in the deformability of red blood cells, leading to more rigid cell membranes, is another manifestation of cross-linking and aminoguanidine has been shown to prevent it in vivo. In such studies, New Zealand White rabbits, with induced, long-term diabetes are used to study the effects of a test compound on red blood cell (RBC) deformability (df). The test compound is administered at a rate of 100 mg/kg by oral gavage (tube delivery to stomach) to diabetic rabbits.

A further consequence of diabetes is the hyperglycemia-induced matrix bone differentiation resulting in decreased bone formation usually associated with chronic diabetes. In animal models, diabetes reduces matrix-induced bone differentiation by 70%.

In the instance where the compositions of the present invention are utilized for in vivo or therapeutic purposes, it can be noted that the compounds or agents used therein are biocompatible. Pharmaceutical compositions can be prepared with a therapeutically effective quantity of the agents or compounds of the present invention and can include a pharmaceutically acceptable carrier, selected from known materials utilized for this purpose. Such compositions can be prepared in a variety of forms, depending on the method of administration. Also, various pharmaceutically acceptable addition salts of the compounds of the invention can be utilized.

Where one or more compounds of formula I are administered to decrease intraocular pressure, at least one compound of formula I administered in effective amount is not a thiazole substituted on a ring carbon with sulfonamide (the amide of which can be substituted) that has carbonic anhydrase inhibiting activity. Of course, the composition can include an effective amount of such an agent, as well as a carbonic anhydrase-inhibiting effective amount of another agent, including one of those distinguished above.

Compounds of the formula I can be conveniently prepared by chemical syntheses well-known in the art. Certain of the compounds are well-known and readily available from chemical supply houses or can be prepared by synthetic methods specifically published therefor. For instance, 4,5-Dimethylthiazole, 4-Methylthiazole, 5-Methylthiazole, 4-Methyl-5-thiazoleethanol, 4-Methyl-5-vinylthiazole, Benzothiazole, 2-Aminobenzothiazole, 2-Amino-4-chlorobenzothiazole, 2-Amino-6-chlorobenzothiazole, 2-Aminothiazole, 2,4,5-Trimethylthiazole, 2-Amino-5-methylthiazole, 2-Amino-4-methylthiazole, 2-Acetylthiazole, 2-Ethyl-4-methylthiazole, Ethyl 2-(Formylamino)-4-thiazoleacetate, 2-(Formylamino)-alpha-(methoxyimino)-4-thiazoleacetic acid, 2-amino-4-phenylthiazole hydrochloride monohydrate, 2-Isobutylthiazole, 2-Methyl-2-thiazoline, 2-Methyl-2-oxazoline, 2-Oxazolidone, Thiomorpholine, 2-Amino-4-thiazoleacetic acid, Imidazole, 1-Methylimidazole, 1-Butylimidazole, 1-Vinylimidazole, 1-Allylimidazole, 1-(Trimethylsilyl) imidazole, 1-(3-Aminopropyl) imidazole, 1-Benzyl imidazole, 1-Phenyl imidazole, 1,5-Dicyclohexyl imidazole, 1 -(p-Toluenesulfonyl) imidazole, N-Benzoyl-imidazole, 4-Methyl-imidazole, 4'-(Imidazol-1-yl)-acetophenone, 4-(Imidazol-1-yl)-phenol, 1-(4-Methoxyphenyl)-1H-imidazol and 1-Methylbenzimidazole can be obtained from Sigma (St. Louis, Mo.), Aldrich (Milwakee, Wis.) or Fluka (Milwaukee, Wis.) (all divisions of Sigma-Aldrich Co.). 1-ethylimidazole can be obtained from TCI America (Portland, Oreg.). N-(Thiazolidinyl)-4-fluoroaniline, N-(Thiazolyl)-2-(4,6-dimethyl-pyrimidin-2-yl-thio)-acetamide, N-(Thiazolyl)-2-(4-propylphenoxy)-acetamide, 2-[4-(N-Furoyl)aminophenyl]-6-methylbenzothiazole, N-(Thiazolyl)-2-(3,5-dimethylphenoxy-acetamide and 2-[(N-(2-Napthalenyl)amino]-[2,3:5,4]-(5,5-dimethyl-cyclohexanonyl)]thiazole can be purchased from MDD, Inc. (Acton, Ontario), a successor to Ortech Corporation.

In one synthetic process to prepare compounds of the general formula I, a thiazole is reacted with an alkyl or acyl halide in the presence of base such as triethylamine, to produce the corresponding alkyl or acyl derivative at the 2 carbon. See, Medici et al., *J. Org. Chem.* 49: 590–596, 1984. In some cases, a chromatographic step is applied to separate additions at the 2 and 3 positions of the thiazole ring.

In another synthesis of compounds of the formula I wherein $R^c$ is amino, nitro-containing analogs of compounds of the invention or precursors thereof are catalytically hydrogenated to the corresponding amino compounds.

2-Amino thiazole compounds wherein ($R^c$ is amino) can also be synthesized by reacting thiourea (which can be substituted on at least one amine) with an alpha-halo ketone using the method described in *Vogel's Textbook of Practical Organic Chemistry*, 5$^{th}$ Edition, John Wiley & Sons, New York, p. 1153. Such a reaction is exemplified by a synthesis of 2-amino-4-phenylthiazole:

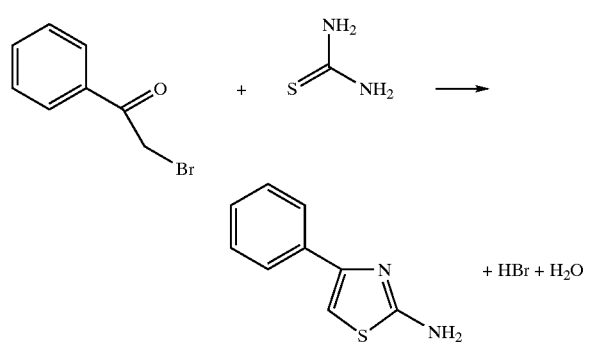

Thiazoles substituted on the ring nitrogen can be prepared by alkylation or acylation with appropriate acyl or alkyl halides.

N-aryl thiazoles and imidazoles can be prepared using appropriate aromatic nucleophilic displacement reactions. For example, fluoro phenyl compounds such as 4-fluorobenzoic acid methyl ester can be used to substitute the $N^1$ nitrogen of imidazole to make methyl-4-(1H-imidazol-1-yl)benzoate. See, Morgan et al., *J. Med. Chem.* 33: 1091–1097, 1990.

Amino functions of 2-aminoimidazoles or 2-aminothiazoles can be acylated by dehydration or other methods known in the art.

Substituted oxazoles can be prepared by methods known in the art. For instance, 2-unsubstituted oxazoles can be formed by condensation of formamide with either α-hydroxy or α-haloketones intermediates (H. Bredereck, R. Gommper, H. G. v. Shuh and G. Theilig, in Newer Methods of Preparative Organic Chemistry, Vol. III, ed. W. Foerst, Academic press, New York, 1964, p. 241). The intermediates can cyclize under acid conditions to form the oxazole ring (Scheme 2). In addition, 2,4-disubstituted oxazoles can be prepared from α-haloketones and amides at higher temperatures using the same method.

Scheme 2

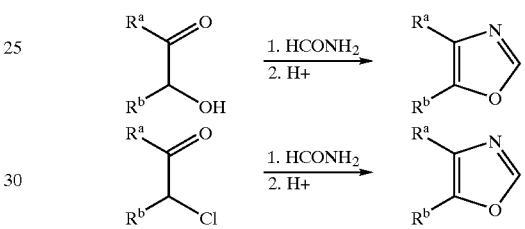

Oxazoles can be prepared by cyclization reactions of isonitriles (van Leusen, A. M. Lect. Heterocycl. Chem. 1980, 5, S111; Walborsky, H. M.; Periasamy, M. P. in *The Chemistry of Functional Groups*, suppl. C, Patai, S.; Rappoport, Z., Eds; Wiley-Interscience, 1983, p. 835; Hoppe, D. *Angew. Chem. Int. Edn. Engl.*, 1974, 13, 789; Schollkopf, U. *Angew. Chem. Int. Ed. Engl.*, 1977, 16, 339). For example, as shown below in Scheme 3, tosylmethyl isocyanide can be deprotonated by a base and reacted with a suitable electrophile (e.g. an aldehyde). The intermediate can cyclize and aromatize to provide the desired oxazole analog. Other methods for preparing oxazoles include 1,5-dipolar cyclization of acylated nitrile ylides (Taylor E. C.; Turchi, I. J. *Chem. Rev.*, 1979, 79, 181; Huisgen, R. *Angew. Chem. Int. Edn. Engl.* 1980, 19, 947)

Scheme 3

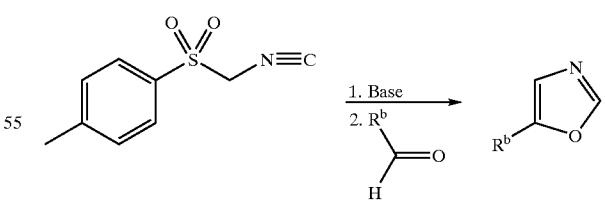

2-Amino-substituted oxazoles (i.e. $R^c$=NH$_2$) can be prepared by two general methods. Urea can be condensed with α-bromo ketones to yield 2-aminooxazoles that can be substituted at the 4 and 5 positions (Scheme 4). Alternatively, another route to 2-aminooxazoles from acyclic precursors is the base catalyzed reaction of cyanamide with α-hydroxy ketones (Scheme 5). 2-Aminooxazoles of the invention can also be prepared from the nucleophilic displacement of amines with 2-chlorooxazole, for example, for compounds of the invention wherein $R^c$ is ArNH— (Gompper, R.; Effenberger, F. *Chem. Ber.,* 1959, 92, 1928).

Scheme 4

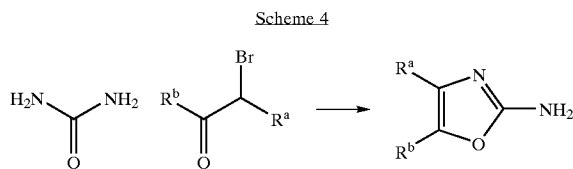

Scheme 5

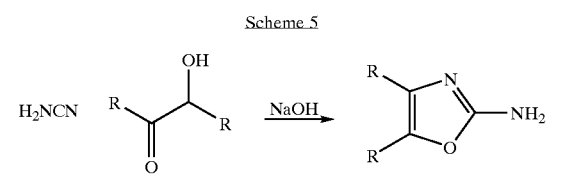

Compounds of the invention, wherein $R^c$ is arylcarbonyl can be synthesized by acylation of the amino moiety of 2-aminooxazoles with, for example, with anhydrides to yield 2-acylaminooxazoles. In addition, 2-aminooxazoles can be acylated, for instance, with chloroacetic anhydride to yield an α-chloro carboxamide. The α-chloro carboxamide can serve as a suitable alkylating reagent that can be treated with, for example, phenols, arylamines and alkylamines to prepare compounds of the invention. An oxazole of the invention wherein $R^c$ is Ar-oxycarbonylamino is shown in Scheme 6.

Scheme 6

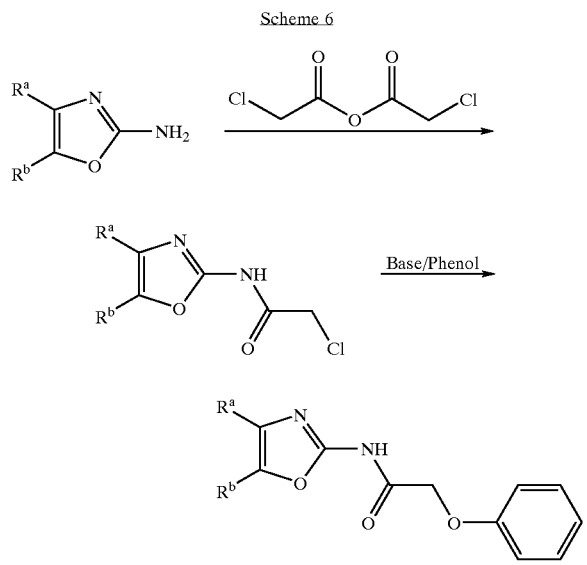

Oxazoles of the invention with $R^c$ is aminocarbonylamino (ureido) or aminothiocarbonylamino (thioureido) can be prepared from 2-aminooxazoles (Scheme 7). 2-Aminooxazoles can be treated with isocyanates and isothiocyanates to yield 2-ureido and 2-thioureido oxazoles, respectively (Crank, G.; Foulis, J. *J. Med. Chem.,* 1971, 14, 1075: Crank, G. Neville, M.; Ryden, R. *J. Med Chem.,* 1974, 16, 1402).

Scheme 7

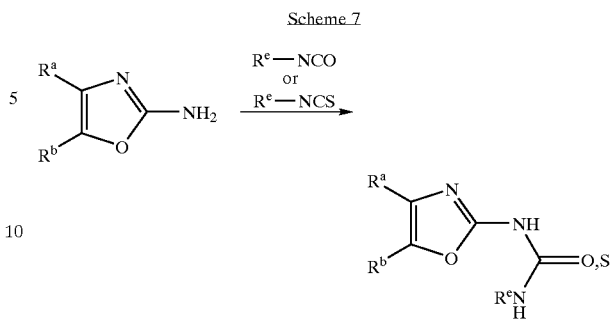

2-Aminooxazoles can be hydrogenated using palladium catalysts to yield 2-aminooxazolines (Scheme 8) (Tanaka, C.; Kuriyama, S. *Yakugaku Zasshi* 1979, 99, 78). 501

Scheme 8

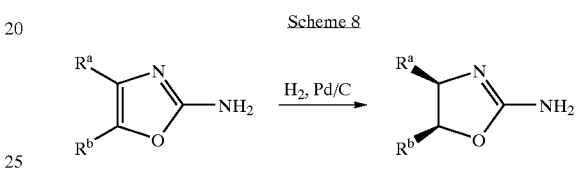

Benzoxazole intermediates substituted at the 2 position can be prepared from 2-aminophenols by acylation with, for example, an acid chloride and cyclization (Scheme 9).

Scheme 9

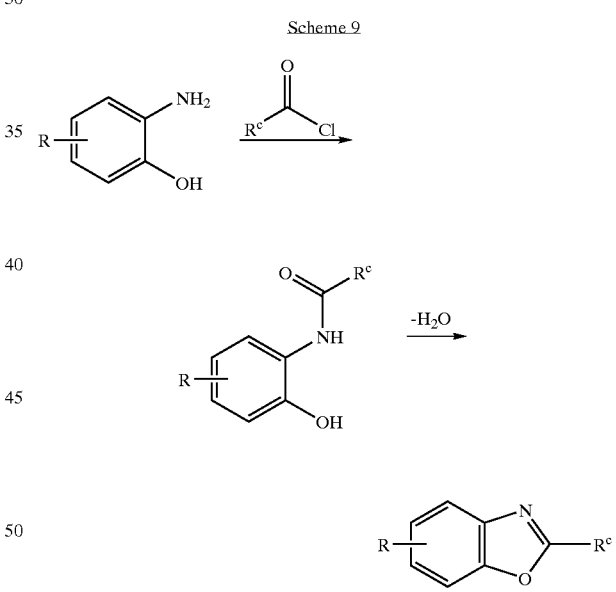

Compounds of the general formula I wherin $R^a$ is hydroxymethyl-, aminomethyl-, alkylaminomethyl, or dialkylaminomethyl- can be prepared from a halomethyl intermediate. In addition cyclic amines such as piperidines, piperazines, and pyrrolidines substituted on a methyl group (i.e., for $R^a$) could also be prepared using the halomethyl intermediate. Compounds of the invention where is 1-imidazolylmethyl- can also be prepared using the same intermediate. A suitable halomethyl intermediate is exemplified in Scheme 10. Those of ordinary skill in the art will note while the intermediate in Scheme 10 is prepared using a thiazole, other substituted thiazoles as well as oxazoles and imidazoles could be prepared analogously.

Scheme 10

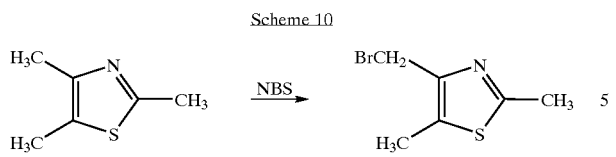

The halomethyl group can be hydrolyzed with, for example, using silver nitrate in water (Scheme 11). Alkylations with amines, including cyclic amines from the same intermediate, are also exemplified.

Scheme 11

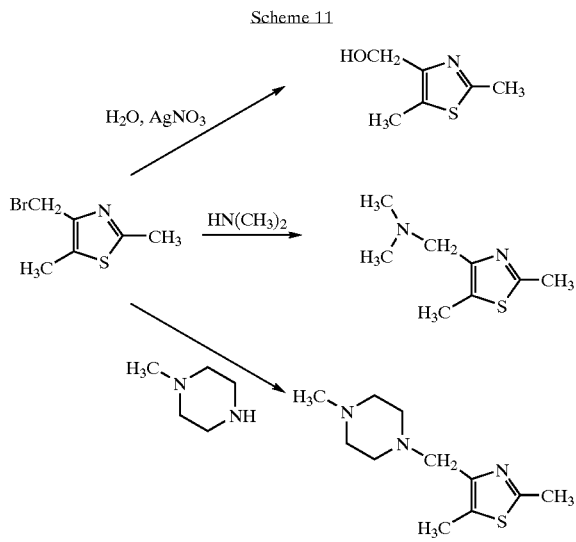

Compounds of the invention where $R^c$ is hydroxymethyl-, amino (or substituted amino) methyl-, cyclic aminomethyl, or N-imidazol-ylmethyl- can be prepared in this manner. For example, a 2-hydroxymethyl thiazole can be chlorinated with for example, thionyl chloride, phosphorus pentachloride, or phosphorus oxychloride to give a chloromethyl intermediate that is a suitable for preparing the above mentioned compounds (Scheme 12). Methods to prepare the compounds wherein $R^c$ is hydroxymethyl and aminomethyl from the chloromethyl intermediate are analogous to those methods illustrated in Scheme 11.

Scheme 12

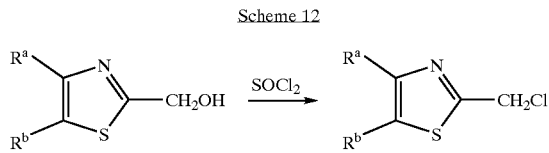

Compounds of the invention wherein $R^c$ is hydroxyethyl-, amino(or substituted amino)ethyl-, cyclic aminoethyl, or N-imidazol-ylethyl- can be prepared from a chloroethyl intermediate (Scheme 13). For instance, a 2-hydroxyethyl thiazole intermediate can be prepared from metalation of a thiazole (or by halogen-metal exchange from a 2-bromothiazole) followed by reaction with ethylene oxide. The resulting 2-hydroxyethylthiazole can be converted to a chloroethylthiazole using a chlorinating agent, such as thionyl chloride. Methods to prepare the compounds wherein $R^c$ is hydroxyethyl and aminoethyl from the chloroethyl intermediate are analogous to those methods illustrated in Scheme 11.

Scheme 13

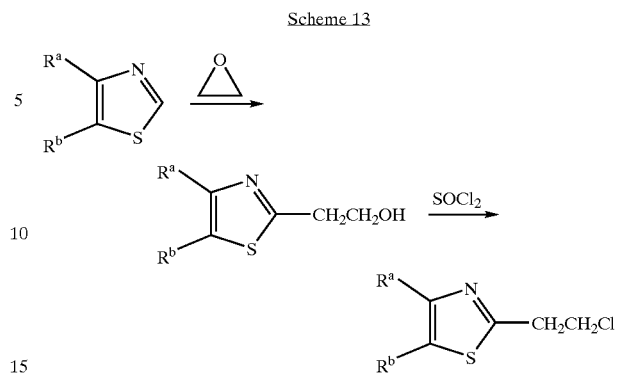

Compounds that can be prepared using the methods depicted in Schemes 10–13 include (2,5-dimethyl-1,3-thiazol-4-yl)methan-1-ol; [(2,5-dimethyl(1,3-thiazol-4-yl)) methyl]dimethylamine; 4-(imidazolylmethyl)-2,5-dimethyl-1,3-thiazole; 2-(imidazolylmethyl)-1,3-thiazole; trimethyl (1,3-thiazol-2-ylmethyl)amine; 2-(2-imidazolylethyl)-1,3-thiazole; dimethyl(2-(1,3-thiazol-2-yl)ethyl)amine; and 2-(2-chloroethyl)-1,3-thiazole.

To treat the indications of the invention, an effective amount of a pharmaceutical compound will be recognized by clinicians but includes an amount effective to treat, reduce, ameliorate, eliminate or prevent one or more symptoms of the disease sought to be treated or the condition sought to be avoided or treated, or to otherwise produce a clinically recognizable change in the pathology of the disease or condition.

Pharmaceutical compositions can be prepared to allow a therapeutically effective quantity of the compound of the present invention, and can include a pharmaceutically acceptable carrier, selected from known materials utilized for this purpose. See, e.g., Remington, The Science and Practice of Pharmacy, 1995; Handbook of Pharmaceutical Excipients, $3^{rd}$ Edition, 1999. Such compositions can be prepared in a variety of forms, depending on the method of administration.

In addition to the subject compound, the compositions of this invention can contain a pharmaceutically-acceptable carrier. The term "pharmaceutically-acceptable carrier", as used herein, means one or more compatible solid or liquid filler diluents or encapsulating substances that are suitable for administration to an animal, including a mammal or human. The term "compatible", as used herein, means that the components of the composition are capable of being commingled with the subject compound, and with each other, such that there is no interaction that would substantially reduce the pharmaceutical efficacy of the composition under ordinary use. Preferably when liquid dose forms are used, the compounds of the invention are soluble in the components of the composition. Pharmaceutically-acceptable carriers must, of course, be of sufficiently high purity and sufficiently low toxicity to render them suitable for administration to the animal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the subject compound is basically determined by the way the compound is to be administered. If the subject compound is to be injected, the preferred pharmaceutically-acceptable carrier is sterile, physiological saline, with a blood-compatible suspending agent, the pH of which has been adjusted to about 7.4.

If the preferred mode of administering the subject compound is perorally, the preferred unit dosage form is therefore tablets, capsules, lozenges, chewable tablets, and the like. Such unit dosage forms comprise a safe and effective amount of the subject compound, which is preferably from about 0.7 or 3.5 mg/ to about 280 mg/ 70 kg, more preferably from about 0.5 or 10 mg to about 210 mg/ 70 kg. The pharmaceutically acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders, such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder-mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of this invention, and can be readily made by a person skilled in the art.

Peroral compositions also include liquid solutions, emulsions, suspensions, and the like. The pharmaceutically-acceptable carriers suitable for preparation of such compositions are well known in the art. Such liquid oral compositions preferably comprise from about 0.012% to about 0.933% of the subject compound, more preferably from about 0.033% to about 0.7%. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. Peroral liquid compositions may also contain one or more components such as sweeteners, flavoring agents and colorants disclosed above.

Other compositions useful for attaining systemic delivery of the subject compounds include sublingual and buccal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

Compositions can also be used to deliver the compound to the site where activity is desired; such as eye drops, gels and creams for ocular disorders.

Compositions of this invention include solutions or emulsions, preferably aqueous solutions or emulsions comprising a safe and effective amount of a subject compound intended for topical intranasal administration. Such compositions preferably comprise from about 0.01% to about 10.0% w/v of a subject compound, more preferably from about 0.1% to about 2.0%. Similar compositions are preferred for systemic delivery of subject compounds by the intranasal route. Compositions intended to deliver the compound systemically by intranasal dosing preferably comprise similar amounts of a subject compound as are determined to be safe and effective by peroral or parenteral administration. Such compositions used for intranasal dosing also typically include safe and effective amounts of preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfite and others; aromatic agents; viscosity adjustors, such as polymers, including cellulose and derivatives thereof; and polyvinyl alcohol and acids and bases to adjust the pH of these aqueous compositions as needed. The compositions may also comprise local anesthetics or other actives. These compositions can be used as sprays, mists, drops, and the like.

Other preferred compositions of this invention include aqueous solutions, suspensions, and dry powders comprising a safe and effective amount of a subject compound intended for atomization and inhalation administration. Such compositions are typically contained in a container with attached atomizing means. Such compositions also typically include propellants such as chlorofluorocarbons 12/11 and 12/114, and more environmentally friendly fluorocarbons, or other nontoxic volatiles; solvents such as water, glycerol and ethanol, these include cosolvents as needed to solvate or suspend the active; stabilizers such as ascorbic acid, sodium metabisulfite; preservatives such as cetylpyridinium chloride and benzalkonium chloride; tonicity adjustors such as sodium chloride; buffers; and flavoring agents such as sodium saccharin. Such compositions are useful for treating respiratory disorders, such as asthma and the like.

Other preferred compositions of this invention include aqueous solutions comprising a safe and effective amount of a subject compound intended for topical intraocular administration. Such compositions preferably comprise from about 0.01% to about 0.8% w/v of a subject compound, more preferably from about 0.05% to about 0.3%. Such compositions also typically include one or more of preservatives, such as benzalkonium chloride or thimerosal; vehicles, such as poloxamers, modified celluloses, povidone and purified water; tonicity adjustors, such as sodium chloride, mannitol and glycerin; buffers such as acetate, citrate, phosphate and borate; antioxidants such as sodium metabisulfite, butylated hydroxy toluene and acetyl cysteine; acids and bases can be used to adjust the pH of these formulations as needed.

Other preferred compositions of this invention useful for peroral administration include solids, such as tablets and capsules, and liquids, such as solutions, suspensions and emulsions (preferably in soft gelatin capsules), comprising a safe and effective amount of a subject compound. Such compositions can be coated by conventional methods, typically with pH or time-dependent coatings, such that the subject compound is released in the gastrointestinal tract at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragi™ coatings, waxes and shellac.

The compounds of the invention are administered by ocular, oral, parenteral, including, for example, using formulations suitable as eye drops. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchromium chloride, and the usual quantities of diluents and/or carriers. See, Remington's Pharmaceutical Sciences, 16th Ed., Mack Publishing, Easton, Pa., 1980, as well as later editions, for information on pharmaceutical compounding.

Numerous additional administration vehicles will be apparent to those of ordinary skill in the art, including without limitation slow release formulations, liposomal formulations and polymeric matrices.

In another preferred embodiment, the pharmaceutically effective amount is approximately 0.1 or 0.5 to 4 mg/kg body weight daily. Still more preferably, the pharmaceutically effective amount is approximately 1 mg/kg body weight daily. In a preferred embodiment, the amount is administered in once daily doses, each dose being approximately 1 mg/kg body weight.

The activity of the compounds of the invention in breaking, reversing or inhibiting the formation of AGE's or AGE-mediated cross-links can be assayed by any of the methods described in U.S. Pat. No. 5,853,703.

The following examples further illustrate the present invention, but of course, should not be construed as in any way limiting its scope.

EXAMPLE

Rats receive a daily intraperitoneal dose of 10 mg/kg of a compound of the invention (n=14) or placebo (n=15) for 30 days. The animals then undergo a thoracotomy and the left anterior descending coronary artery iss ligated. The chest is then closed and the animals allowed to recover for 14 days while continuing to be treated with compound or placebo. The animals are then sacrificed and the hearts removed for histological examination. The weight of the infarcted tissue was is measured for the placebo treated animals and compared to the weight for the compound treated animals. The thickness of the ventricular wall in the infarcted zone in compound-treated animals is compared to placebo.

Example 1

2,6-diamino-benzothiazole dihydrochloride: 4 g of 2-amino-6-nitrobenzothiazole (Aldrich) was suspended in 130 ml MeOH, and 0.4 g 10% Pd/C (Aldrich) added. The suspension was hydrogenated at room temperature under 60 psi $H_2$ for 6.5 h. The reaction mixture was filtered, and the particulate washed with MeOH. The filtrate was concentrated under reduced pressure, and crystals formed from the concentrate were collected to yield 2.67 g, mp 196-198° C, yield 81.6%. 0.91 g of this product was dissolved in 22 ml MeOH, and the pH adjusted with HCl to 4 to produce 1.2 g of crystals of 2,6-diamino-benzothiazole dihydrochloride. mp 318-320° C, 92.3% yield. Anal. calc. for $C_7H_9N_3SCl_2$, C 35.30%, H 3.80%, N 17.64%. Found, C 34.91%, H 3.67%, N 17.71%.

Example 2

2-(3,5-Dimethylphenoxy)-N-thiazol-2-yl)acetamide: First Route: 3,5-Dimethylphenol is reacted with bromoacetic acid at 110° C. for four hours, with the reaction mixture stirred overnight without added heat. The resulting (3,5-dimethylphenoxy)acetic acid is dissolved in methylene chloride and coupled to 2-aminothiazole in an overnight, room temperature reaction conducted in the presence of base (N-methylmorpholine) and dehydration mediators 1-hydroxybenzotriazole and 1-(3-dimethylaminopropyl)-3-ethyl-carbodiimide hydrochloride.

Second Route: 3,5-Dimethylphenol is reacted for 4.5 h with bromoacetic acid in THF under nitrogen and in the presence of sodium hydride. The resulting (3,5-dimethylphenoxy)acetic acid is reacted overnight with thionyl chloride, with heat. The resulting (3,5-dimethylphenoxy) acetyl chloride is reacted overnight with 2-aminothiazole in the presence of triethylamine, with cooling to 0° C.

Third Route: 2-Aminothiazole (20 g, 199.7 mmol) was suspended in methylene chloride (200 ml), in the presence of pyridine (20 ml, ~250 mmol), and the mixture cooled to 0° C. Bromoacetyl bromide (18.1 ml, 207.6 mmol) was dissolved in 400 ml methylene chloride, and this solution added to the suspended 2-aminothiazole dropwise. The resulting reaction mixture was stirred at room temperature overnight. The crude product was washed with water (200 ml, 1×), then sodium bicarbonate solution (200 ml, 2×), dried over $Na_2SO_4$, filtered, and evaporated. The product 2-bromoacetamidothiazole was crystallized from MeOH. Yield, 4 g, mp 148° C.

A solution of 3,5-dimethylphenol (2.5g, 13.9 mmol) in dry DMF (20 ml) was placed under a dry nitrogen atmosphere. Sodium hydride (0.7 g, 27.8 mmol; a 60% dispersion in mineral oil) was added in portions, and the mixture stirred for 1 h. A solution of 2-bromoacetamidothiazole (3.0 g, 13.9 mmol) in dry DMF (10 ml) was added to the mixture dropwise. The reaction was heated to 90° C. for 5 h, then maintained overnight without external heat. The reaction mixture was poured into ice water, and the resulting material extracted with methylene chloride (50 ml×3). The organic layer was washed with water (100 ml×5), dried over $Na_2SO_4$, filtered, and evaporated. The residue from evaporation was purified by silica gel chromatography developed with pet. ether:ether (1:1 v/v). The product 2-(3,5-dimethylphenoxy)-N-thiazol-2-yl)acetamide [N-(thiazolyl)-2-(3,5-dimethylphenoxy)-acetamide] was crystallized from acetonitrile and methyl tert-butyl ether. Yield, 1.04 g, mp 124–125° C.

The compounds 2-(3,5-dimethylphenoxy)-N-(4-methyl (1,3-thiazol-2-yl))acetamide, 2-(3,5-dimethylphenoxy)-N-(5-methyl(1,3-thiazol-2-yl))acetamide, N-(4,5-dimethyl(1,3-thiazol-2-yl))-2-(3,5-dimethylphenoxy)acetamide, 2-(3,5-dimethylphenoxy)-N-[5-(2-hydroxyethyl)-4-methyl(1,3-thiazol-2-yl)]acetamide, 2-(3,5-dimethylphenoxy)-N-(5-chloro(1,3-thiazol-2-yl))acetamide, N-benzothiazol-2-yl-2-(3,5-dimethylphenoxy)acetamide, 2-(3,5-dimethylphenoxy)-N-(5-bromo(1,3-thiazol-2-yl))acetamide, 2-(3,5-dimethylphenoxy)-N-(4-phenyl(1,3-thiazol-2-yl))acetamide, ethyl 2-[2-(3,5-dimethylphenoxy)acetylamino]-4-phenyl-1,3-thiazole-5-carboxylate, 2-(3,5-dimethylphenoxy)-N-5-nitro(1,3-thiazol-2-yl))acetamide, 2-(3,5-dimethylphenoxy)-N-(6-nitrobenzothiazol-2-yl) acetamide, ethyl 2-[2-(3,5-dimethlylphenoxy)acetylamino]-1,3-thiazole-4-carboxylate, 2-(3,5-dimethylphenoxy)-N-(1-methylimidazol-2-yl)acetamide, 2-(3,5-dimethylphenoxy)-N-(1-methylbenzimidazol-2-yl)acetamide, 2-(3,5- dimethylphenoxy)-N-[1-benzylbenzimidazol-2-yl] acetamide and 2-(3,5-dimethylphenoxy)-N-(5-chlorobenzoxazol-2-yl)acetamide are made by one or more of the same methods, with the 2-amino heterocycle substituted as appropriate to obtain the product.

Example 3

2-Furyl-N-[4-(6-methyl-benzothiazol-2-yl)phenyl] carboxamide: First Route: 2-Furoic acid (1.85 g, 16.5 mmole) was dissolved in anhydrous methylene chloride (30 ml), to which solution was added a suspension of 2-(4-amino-phenyl)-6-methyl benzothiazole (4.76 g, 16.5 mmole) and N-methyl morpholine (2.0 g, 16.5 mmole) in methylene chloride (30 ml, at room temperature). Then, 1-hydroxy-benzotriazole hydrate (2.67 g, 16.5 mmole) and 1-(3-dimethyl amino propyl)-3-ethyl carbodiimide hydrochloride (4.75 g, 16.5 mmole) were added at room temperature. More methylene chloride (20 ml.) was added with stirring at room temperature, and the reaction maintained overnight. The initial clear reaction solution changed to a turbid solution. More methylene chloride (10 ml.) was added to the product mixture, which was then extracted with 1N HCl to separate a solid. The solid was filtered and washed with water. The product solid was crystallized from large amount of MeOH to yield 2.19 g (33.1%). mp 238–240° C. $^1$H and $^{13}$C NMR were consistent with the expected product. TLC showed one spot (5% MeOH-CH$_2$Cl$_2$ as developing solvent on silica gel plate).

Route 2: 2-(4-aminophenyl)-6-methyl benzothiazole (2.0 g, 8.3 mmole) and 2-Furoyl chloride (1.086 g, 8.32 mmole) were suspended in methylene chloride (30 ml, anhydrous). triethylamine (1.24 g, 12.25 mmole) was added to the reaction mixture with stirring at room temperature for 2 days. (pH 7.0-7.2). Methylene chloride (50 ml) was added to the reaction mixture, and the reaction mixture extracted with 1 N HCl (50 ml) to separate a solid. The solid was filtered and washed with water to yield 1.3 g (46%) of the desired compound. The product was crystallized from MeOH to obtain 0.99 g, mp 238–240° C. $^1$H and $^{13}$C NMR were consistent with the expected product. TLC showed one spot (5% MeOH-CH$_2$Cl$_2$ as developing solvent on silica gel plate).

Definitions

Heterocycle. Except where heteroaryl is separately recited for the same substituent, the term "heterocycle" includes heteroaryl.

All publications and references, including but not limited to patents and patent applications, cited in this specification are herein incorporated by reference in their entirety as if each individual publication or reference were specifically and individually indicated to be incorporated by reference herein as being filly set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A method of, treating damage to blood vasculature, atherosclerosis, peripheral vascular disease, coronary heart disease or heart failure in an animal, comprising administering an effective amount of a compound of formula I or IA,

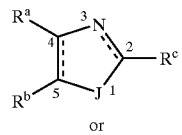

I or

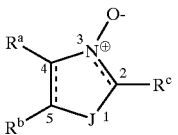

IA wherein:

a. J is sulfur;

b. the carbon 2 to nitrogen bond is a double bond except when R$^c$ is oxo;

c. the bond between carbons 4 and 5 is a single bond or a double bond;

d. R$^a$ and R$^b$ are
   1. independently selected from hydrogen, acylamino, acyloxyalkyl, alkanoyl, alkanoylalkyl, alkenyl, alkoxy, alkoxycarbonyl, alkoxycarbonylalkyl, alkyl, alkylamino, allyl, amino, ω-alkylenesulfonic acid, carbamoyl, carboxy, carboxyalkyl (which alkyl can be substituted with alkyloxyimino), cycloalkyl, dialkylamino, halo, hydroxy, (C$_2$–C$_6$)hydroxyalkyl, mercapto, nitro, sulfamoyl, sulfonic acid, alkylsulfonyl, alkylsulfinyl, alkylthio, trifluoromethyl; or
   2. together with their ring carbons form a C$_6$- or C$_{10}$-aryl fused ring; or
   3. together with their ring carbons form a C$_5$–C$_7$ fused cycloalkyl ring having up to two double bonds including a fused double bond of the containing group, which cycloalkyl ring can be substituted by one or more of the group consisting of alkyl alkoxycarbonyl, amino, aminocarbonyl, carboxy, fluoro, or oxo.

e. R$^c$ is
   1. oxo (when $\Delta^{2,3}$ is not present), or (when $\Delta^{2,3}$ is present) hydrogen, alkyl, alkylthio, hydrogen, mercapto, amino, amino (C$_1$–C$_5$) alkyl, amino(C$_6$ or C$_{10}$)aryl, or wherein the amino of the last three groups can be substituted with
      (a) Ar,
      (b) Ar—Z—, Ar-alkyl-Z—, Ar—Z-alkyl, Ar-amino-Z-, Ar-aminoalkyl-Z-, or Ar- oxyalkyl-Z-, wherein Z is a carbonyl or —SO$_2$—
      (c) formyl or alkanoyl, or
      (d) up to two alkyl,
   2. —NHC(O)(CH$_2$)$_n$—D—R$^e$R$^f$, wherein D is oxygen, sulfur or nitrogen, wherein where D is nitrogen n is 0, 1 or 2, but when D is oxygen or sulfur n=1 or 2, and R$^f$ is present only when D is nitrogen, wherein
      (a) R$^e$ is
         (1) Ar,
         (2) a C$_3$–C$_8$ cycloalkyl ring having up to one double bond with the proviso that the carbon linking the cyloalkyl ring to D is saturated, which cycloalkyl ring can be substituted by one or more alkyl-, alkcoxycarbonyl-, amino-, aminocarbonyl-, carboxy-, fluoro-, or oxo-substituents;
(3) hydrogen, (C$_2$–C$_6$)hydroxyalkyl, alkanoylalkyl, alkyl, alkoxycarbonylalkyl, alkenyl, carboxyalkyl (which alkyl can be substituted with alkoxyimino), alkoxycarbonyl, a group Ar$^\Phi$ which is C$_6$- or C$_{10}$- aryl or Ar$^\Phi$-alkyl; and
(b) R$^f$ is independently hydrogen, (C$_2$–C$_6$) hydroxyalkyl, alkanoylalkyl, alkyl, alkoxycarbonylalkyl, alkenyl, carboxyalkyl (which alkyl can be substituted with alkyloxyimino), alkoxycarbonyl, Ar$^\Phi$, or Ar$^\Phi$-alkyl;

wherein aryl, Ar, or Ar$^\Phi$ can be substituted with, in addition to any substitutions specifically noted one or more substituents selected from the group of acylamino, acyloxyalkyl, alkanoyl, alkanoylalkyl, alkenyl, alkoxy, alkoxycarbonyl, alkoxycarbonylalkyl, alkyl, alkylamino, alkylsulfonyl, alkylsulfinyl, Φ-alkylenesulfonic acid, alkylthio, allyl, amino, ArC(O)-, ArC(O)NH-, carboxy, carboxyalkyl, cycloalkyl, dialkylamino, halo, trifluoromethyl, hydroxy, (C$_2$–C$_6$) hydroxyalkyl, mercapto, nitro, ArO—, Ar-, Ar-alkyl-, sulfamoyl, sulfonic acid, except those of Ar and A$^\Phi$, can be substituted with in addition to any substitutions specifically noted one or more substituents selected from acylamino, alkanoyl, alkoxy, alkoxycarbonyl, alkoxycarbonylalkyl, alkyl, alkylsulfonyl, alkylsulfinyl, alkylthio, amino, ArC(O)—, ArO—, Ar-, Ar-alkyl, carboxy, dialkylamino, fluoro, fluoroalkyl, difluoroalkyl, hydroxy, mercapto, oxo, sulfamoyl, and trifluoromethyl; or a pharmaceutically acceptable salt of said compounds.

2. The method of claim 1, comprising administering an effective amount of a compound of the formula I, wherein J is S, and R$^c$ is hydrogen, oxo, alkyl, amino, amino(C$_1$–C$_5$)alkyl or aminophenyl, wherein the amino of the latter three groups can be substituted with
(a) Ar;
(b) Ar—Z—, Ar-alkyl-Z—, Ar—Z-alkyl, Ar-amino-Z-, Ar-aminoalkyl-Z-, or Ar-oxyalkyl-Z-, wherein Z is a carbonyl or —SO—; or
(c) formyl or alkanoyl.

3. The method of claim 1, comprising administering an effective amount of a compound of the formula I wherein J is S, and R$^c$ is hydrogen, oxo, alkyl, amino, amino(C$_1$–C$_5$)alkyl or aminophenyl, wherein the amino of the latter three groups can be substituted with
(a) Ar;
(b) Ar—Z—, Ar-alkyl-Z—, Ar—Z-alkyl, Ar-amino-Z-, Ar-aminoalkyl-Z-, or Ar-oxyalkyl-Z-, wherein Z is a carbonyl or —SO$_2$—; or
(c) formyl or alkanoyl.

4. The method of claim 1, comprising administering an effective amount of a compound of the formula I, wherein the compound is selected from the group consisting of thiazole; 2-amino-4-chlorobenzothiazo; 2,4,5-trimethylthiazole; 2-(3,5- dimethylphenoxy)-N-thiazol-2-yl)acetamide-; 2-isobutylthiazol; (4-fluorophenyl)thiazolin-2-ylamine; and 5,5-dimethyl-2-(2-naphthylamino)-4,5,6-trihydrobenzothiazol-7-one.

5. The method of claim 1, comprising administering an effective amount of a compound of the formula I, wherein R$^a$ and R$^b$ are 1. independently selected from hydrogen, acylamino, alkanoyl, alkanoylalkyl, alkoxy, alkoxycarbonyl, alkoxycarbonylalkyl, alkyl, alkylamino, amino, Φ-alkylenesulfonic acid, carbamoyl, carboxy, carboxyalkyl (which alkyl can be substituted with alkyloxyimino), cycloalkyl, dialkylamino, halo, hydroxy, (C$_2$–C$_6$)hydroxyalkyl, mercapto, nitro, sulfamoyl, sulfonic acid, alkylsulfonyl, alkylsulfinyl, alkylthio and trifluoromethyl; or
2. together with their ring carbons form a C$_6$- or C$_{10}$-aryl fused ring; or
3. together with their ring carbons form a C$_5$–C$_7$ fused cycloalkyl ring having no double bonds except a fused double bond of the formula I or IA ring, which cycloalkyl ring can be substituted by one or more of the group consisting of alkyl, amino, aminocarbonyl, carboxy, fluoro, or oxo, where multiple substituents are located on different carbon atoms of the cycloalkyl ring, except in the case of alkyl and fluoro substituents, which can be located on the same or different carbon atoms.

6. A method of, damage to blood vasculature, atherosclerosis, peripheral vascular disease, coronary heart disease or heart failure, in an amimal, comprising administering an effective amount of a compound of formula III:

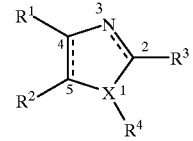

wherein:
X is sulfur; the carbon 2 to nitrogen bond is a double bond except when R$^3$ is oxo; the bond between carbons 4 and 5 is a single bond or a double bond;
R$^1$ and R$^2$
are independently hydrogen, hydroxyalkyl, (C$_2$–C$_6$) alkanoylalkyl, alkyl, alkoxycarbonylalkyl, alkenyl, carboxyalkyl (which alkyl can be substituted with alkyloxyimino), alkoxycarbonyl, or
together with their ring carbons form a C$_6$–C$_{10}$ aromatic fused ring which can be substituted by one or more halo, amino, alkyl, sulfo, or sulfoalkyl; groups, or
together with their ring carbons form a C$_5$–C$_7$ fused cycloalkyl or cycloalkenyl ring having up to two double bonds including a fused double bond of the thiazole radical, which aliphatic ring can be substituted by one or more amino, halo, alkyl, sulfo, sulfoalkyl, carboxy, carboxyalkyl, or oxo groups;
R$^3$ is
(a) when X is S, R$^3$ is hydrogen, oxo, alkyl, amino, amino(C$_1$–C$_5$)alkyl or aminophenyl, wherein the amino of the latter three groups can be substituted with:
(i) Ar,
(ii) Ar-carbonyl, Ar-alkanoyl, Ar-carbonylalkyl, Ar-aminocarbonyl Ar-aminoalkanoyl or Ar-oxyalkanoyl or
(iii) formyl or alkanoyl,
(b) —NHC(O)(CH$_2$)$_n$—Y—R$^5$R$^6$, wherein Y is oxygen, sulfur or nitrogen, n is 0 or 1, but n=1 when Y is oxygen or sulfur, and $R^6$ is present only when Y is nitrogen, wherein $R^5$ is
(i) Ar,
(iii) a $C_3$–$C_8$ cycloalkyl or cycloalkenyl ring having up to one double bond, which aliphatic ring can be substituted by one or more amino, halo, alkyl, sulfo, sulfoalkyl, carboxy, carboxyalkyl, or oxo groups;
(v) hydrogen, hydroxyalkyl, ($C_2$–$C_6$) alkanoylalkyl, alkyl, alkoxycarbonylalkyl, alkenyl, carboxyalkyl (which alkyl can be substituted with alkyloxyimino), alkoxycarbonyl, a group Ar which is ($C_6$–$C_{10}$) aryl or Ar-alkyl, and $R^6$ is independently hydrogen, hydroxyalkyl, ($C_2$–$C_6$)alkanoylalkyl, alkyl, alkoxycarbonylalkyl, alkenyl, carboxyalkyl (which alkyl can be substituted with alkyloxyimino), alkoxycarbonyl, a group Ar which is ($C_6$–$C_{10}$) aryl Ar-alkyl;

wherein each group Ar can be substituted by one or more halo, amino, alkyl, alkoxy, alkoxycarbonyl, sulfo, or sulfoalkyl, groups, or a pharmaceutically acceptable salt of said compounds.

7. The method of claim 6, comprising administering an amount effective therefor of one or more compounds of the following formula:

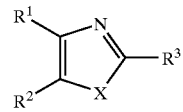

V wherein $R^1$, $R^2$ and $R^3$ are defined in claim 1.

8. The method of claim 6, comprising administering an amount effective therefor of one or more compounds of the following formula:

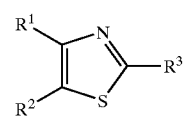

VI wherein $R^1$, $R^2$ and $R^3$ are defined in claim 1.

9. The method of claim 1 or 6, wherein the animal is human.

10. The method of claim 1 or 6, where formation of advanced glycosylation end products in the animal is inhibited, or preformation of advanced glycosylation end products in the animals is reversed.

* * * * *

UNITED STATES PATENT AND TRADEMARK OFFICE
CERTIFICATE OF CORRECTION

PATENT NO. : 6,960,605 B2
DATED : November 1, 2005
INVENTOR(S) : Dilip Wagle, Sarah Vasan and Jack Egan It is certified that error appears in the above-identified patent and that said Letters Patent is hereby corrected as shown below:

Column 31,
Line 64, "method of, treating" should read -- method of treating --.

Column 33,
Line 22, "Φ-alkylenesulfonic acid" should read -- ω-alkylenesulfonic acid --.
Line 26, "sulfamoyl, sulfonic" should read -- sulfamoyl, and sulfonic --.
Line 26, "$A^{Φ}$" should read -- $Ar^{Φ}$ --.
Line 30, "alkyl, alkylsulfonyl" should read -- alkyl, alkylamino, alkylsulfonyl --.
Line 44, "-SO-" should read -- $-SO_2-$ --.
Line 60, "2-amino-4-chlorobenzothiazo" should read
-- 2-amino-4-chlorobenzothiazole --.
Line 62, "2-isobutylthiazol" should read -- 2-isobutylthiazole --.

Column 34,
Line 4, "Φ-alkylenesulfonic acid" should read -- ω-alkylenesulfonic acid --.
Line 24, "method of, damage" should read -- method of treating damage --.
Line 26, "amimal" should read -- animal --.

Column 35,
Line 4, "(iii)" should read -- (ii) --.
Line 10, "(v)" should read -- (iii) --.

Column 36,
Line 26, "animals" should read -- animal --.
Line 27, claim 11 should be added -- The method of claim 6, comprising administering an amount effective therefore of one or more compounds of formula III, wherein each Ar or cycloalkyl group is substituted with up to two substituents --.

Signed and Sealed this

Seventh Day of February, 2006

JON W. DUDAS
*Director of the United States Patent and Trademark Office*